(12) United States Patent
Kotewicz et al.

(10) Patent No.: US 6,610,522 B1
(45) Date of Patent: *Aug. 26, 2003

(54) CLONED GENES ENCODING REVERSE TRANSCRIPTASE LACKING RNASE H ACTIVITY

(75) Inventors: Michael Leslie Kotewicz, Columbia, MD (US); Gary Floyd Gerard, Frederick, MD (US)

(73) Assignee: Invitrogen Corporation, Carlsbad, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/220,330

(22) Filed: Dec. 24, 1998

Related U.S. Application Data

(63) Continuation of application No. 08/798,458, filed on Feb. 10, 1997, now Pat. No. 6,063,608, which is a continuation of application No. 08/614,260, filed on Mar. 12, 1996, now Pat. No. 5,668,005, which is a continuation of application No. 08/404,907, filed on Mar. 15, 1995, now abandoned, which is a continuation of application No. 07/825,260, filed on Jan. 24, 1992, now Pat. No. 5,405,776, which is a division of application No. 07/671,156, filed on Mar. 18, 1991, now Pat. No. 5,244,797, which is a continuation of application No. 07/143,396, filed on Jan. 13, 1988, now abandoned.

(51) Int. Cl.$^7$ .......................... C12N 9/12; C12N 15/54; C12N 15/70; C12P 19/34
(52) U.S. Cl. ................ 435/194; 435/69.1; 435/91.1; 435/91.2; 435/252.33; 435/252.3; 435/320.1; 435/471; 536/23.2
(58) Field of Search ................ 536/23.2; 435/194, 435/69.1, 252.3, 252.33, 320.1, 91.1, 91.2, 475, 975, 471

(56) References Cited

U.S. PATENT DOCUMENTS

| | | | |
|---|---|---|---|
| 4,663,290 A | 5/1987 | Weis et al. | 435/253 |
| 4,795,699 A | 1/1989 | Tabor et al. | 435/5 |
| 4,943,531 A | * 7/1990 | Goff et al. | 435/194 |

(List continued on next page.)

FOREIGN PATENT DOCUMENTS

| | | |
|---|---|---|
| WO | WO 86/06741 | 11/1986 |

OTHER PUBLICATIONS

Hizi, A., et al., 1989, "Effects of small insertions on the RNA–dependent DNA polymerase activity of HIV–1 reverse transcriptase", Virology, vol. 170, pp. 326–329.*

(List continued on next page.)

*Primary Examiner*—Ponnathapu Achutamurthy
*Assistant Examiner*—William W. Moore
(74) *Attorney, Agent, or Firm*—Sterne, Kessler, Goldstein & Fox P.L.L.C.

(57) ABSTRACT

The invention relates to a gene which encodes reverse transcriptase having DNA polymerase activity and substantially no RNase H activity. The invention also relates to vectors containing the gene and hosts transformed with the vectors of the invention. The invention also relates to a method of producing reverse transcriptase having DNA polymerase activity and substantially no RNase H activity by expressing the reverse transcriptase genes of the present invention in a host. The invention also relates to a method of producing cDNA from mRNA using the reverse transcriptase of the invention. The invention also relates to a kit for the preparation of cDNA from mRNA comprising the reverse transcriptase of the invention.

98 Claims, 8 Drawing Sheets

U.S. PATENT DOCUMENTS

| | | | | |
|---|---|---|---|---|
| 5,017,488 | A | | 5/1991 | McAllister et al. .......... 435/194 |
| 5,017,492 | A | | 5/1991 | Kotewicz et al. ......... 435/252.3 |
| 5,244,797 | A | * | 9/1993 | Kotewicz et al. ............ 435/194 |
| 5,405,776 | A | * | 4/1995 | Kotewicz et al. .......... 435/69.1 |
| 5,668,005 | A | * | 9/1997 | Kotewicz et al. ............ 435/194 |
| 6,063,608 | A | | 5/2000 | Kotewicz et al. ............ 435/194 |

OTHER PUBLICATIONS

Hizi, A., et al., 1991, "Mutational analysis of the DNA polymerase and ribonuclease H activities of human immunodeficiency virus yype 2 reverse transcriptase expressed in *Escherichia coli*", Virology, vol. 180, pp. 339–346.*

Hostomsky, Z., et al., 1991, "Reconstitution in vitro of RNase H activity using purified N–terminal and C–terminal domains of human immunodeficiency virus type 1 reverse transcriptase", Proceedings, Nat'l Academy of Sciences, U.S.A., vol. 88, pp. 1148–1152.*

Akins, R.A. et al., "Mitochondrial Plasmids of Neurospora: Integration into Mitochondrial DNA and Evidence for Reverse Transcription in Mitochondria," *Cell* 47:505–516 (1986).

Bassin, R.H. et al., "Macromolecular Requirements for Abrogation of Fv–1 Restriction by Murine Leukemia Viruses," *J. Virology* 35(2):287–297 (1980).

Berger, S.L. et al., "Reverse Transcriptase and Its Associated Ribonuclease H: Interplay of Two Enzyme Activities Controls the Yield of Single–Stranded Complementary Deoxyribonucleic Acid," *Biochemistry* 23:2365–2372 (1983).

Blain, S.W. and Goff, S.P., "Nuclease Activities of Moloney Murine Leukemia Virus Reverse Transcriptase," *J. Biol. Chem.* 268(31):23585–23592 (1993).

Carter, P. and Wells, J.A., "Engineering Enzyme Specificity by 'Substrate–Assisted Catalysis,'" *Science* 237:394–399 (1987).

Fawcett, D.H. et al., "Transposable Elements Controlling I–R Hybrid Dysgenesis in *D. melanogaster* Are Similar to Mammalian LINEs," *Cell* 47:1007–1015 (1986).

Finston, W.I. and Champoux, J.J., "RNA–Primed Initiation of Moloney Murine Leukemia Virus Plus Strands by Reverse Transcriptase In Vitro," *J. Virology* 51(1):26–33 (1984).

Gerard, G.F. et al., "Poly (2'–0–methylcytidylate) Oligodeoxyguanylate as a Template for the Ribonucleic Acid Directed Deoxyribonucleic Acid Polymerase in Ribonucleic Acid Tumor Virus Particles and a Specific Probe for the Ribonucleic Acid Directed Enzyme in Transformed Murine Cells," *Biochemistry* 13(8):1632–1641 (1974).

Gerard, G.F. and Grandgenett, D.P., "Purification and Characterization of the DNA Polymerase and RNase H Activities in Moloney Murine Sarcoma–Leukemia Virus," *J. Virology* 15(4):785–797 (1975).

Gerard, G.F., "Multiple RNase H Activities in Mammalian Type C Retravirus Lysates," *J. Virology* 26(1):16–28 (1978).

Gerard, G.F., "Mechanism of Action of Moloney Murine Leukemia Virus RNase H III" *J. Virology* 37(2):748–754 (1981).

Gerard, G.F. et al., "Influence on Stability in *Escherichia coli* of the Carboxy–Terminal Structure of Cloned Moloney Murine Leukemia Virus Reverse Transcriptase," *DNA* 5(4):271–279 (1986).

Gerwin, B.I. et al., "Mutant of B–Tropic Murine Leukemia Virus Synthesizing an Altered Polymerase Molecule," *J. Virology* 31(3):741–751 (1979).

Gorecki, M. and Panet, A., "Discrimination of DNA Polymerase and RNase H Activities in Reverse Transcriptase of Avian Myeloblastosis Virus," *Biochemistry* 17(12):2438–2442 (1978).

Johnson, M.S. et al., "Computer analysis of retroviral pol genes: Assignment of enzymatic functions to specific sequences and homologies with nonviral enzymes," *Proc. Natl. Acad. Sci. USA* 83(20):7648–7652 (1986).

Kamer, G. and Argos, P., "Primary structural comparison of RNA–dependent polymerases from plant, animal and bacterial viruses," *Nucl. Acids. Res.* 12(18):7269–7282 (1984).

Kotewicz, M.L. et al., "Cloning and overexpression of Moloney murine leukemia virus reverse transcriptase in *Escherichia coli*," *Gene* 35:249–258 (1985).

Kotewicz, M.L. et al., "Isolation of cloned Moloney murine leukemia virus reverse transcriptase lacking ribonuclease H activity," *Nucl. Acids Res.* 16(1):265–277 (1988).

Lai, M.–H.T. and Verma, I.M., "Reverse Transcriptase of RNA Tumor Viruses. V. In Vitro Proteolysis of Reverse Transcriptase from Avian Myeloblastosis Virus and Isolation of a Polypeptide Manifesting Only RNase H Activity," *J. Virology* 25(2):652–663 (1978).

Lai, M.–H.T. et al., "Mammalian Retrovirus–Associated RNase H Is Virus Coded," *J. Virology* 27(3):823–825 (1978).

Levin, J.G. et al., "Murine Leukemia Virus Mutant with a Frameshift in the Reverse Transcriptase Coding Region: Implication for pol Gene Structure," *J. Virology* 51(2):470–478 (1984).

Maniatis, T. In: *Molecular Cloning, A Laboratory Manual*, Cold Spring Harbor Laboratory Press, pp. 213 and 231 (1982).

Meloun, B. et al., "Complete primary structure of thermitase from *Thermoatinomyces vulgaris* and its structural features related to the subtilisin–type proteinases," *FEBS Letters* 183(2):195–200 (1985).

Messer, L.I. et al., "Functional Analysis of Reverse Transcription by a Frameshift pol Mutant of Murine Leukemia Virus," *Virology* 146:146–152 (1985).

Michel, F. and Lang, B.F., "Mitochondrial class II introns encode proteins related to the reverse transcriptases of retroviruses," *Nature* 316:641–643 (1985).

Moelling, K. and Friis, R.R., "Two Avian Sarcoma Virus Mutants with Defects in the DNA Polymerase–RNase H Complex," *J. Virology* 32(2):370–378 (1979).

Resnick, R. et al., "Involvement of Retrovirus Reverse Transcriptase–Associated RNase H in the Initiation of Strong–Stop (+) DNA Synthesis and the Generation of the Long Terminal Repeat," *J. Virology* 51(3):813–821 (1984).

Roth, M.J. et al., "Purification and Characterization of Murine Retroviral Reverse Transcriptase Expressed in *Escherichia coli*," *J. Biol. Chem.* 260(16):9326–9335 (1985).

Shinnick, T.M. et al., "Nucleotide sequence of Moloney murine leukaemia virus," *Nature* 293:543–548 (1981).

Smith, J.K. et al., "Initiation of Plus–Strand DNA Synthesis During Reverse Transcription of an Avian Retrovirus Genome," *J. Virology* 49(1):200–204 (1984).

Tanese, N. et al., "Analysis of Retroviral pol Gene Products with Antisera Raised against Fusion Proteins Produced in *Escherichia coli*," *J. Virology* 59(2):328–340 (1986).

Tanese, N. et al., "Expression of enzymatically active reverse transcriptase in *Escherichia coli*," *Proc. Natl. Acad. Sci. USA* 82(15):4944–4948 (1985).

Telesnitsky, A. and Goff, S.P., "RNase H domain mutations affect the interaction between Moloney murine leukemia virus reverse transcriptase and its primer–template," *Proc. Natl. Acad. Sci. USA* 90:1276–1280 (1993).

Toh, H. et al., "Sequence homology between retroviral reverse transcriptase and putative polymerases of hepatitis B virus and cauliflower mosaic virus," *Nature* 305:827–829 (1983).

Tronick, S. R. et al., "Molecular cloning of Moloney murine sarcoma virus: Arrangement of virus–related sequences within the normal mouse genome," *Proc. Natl. Acad. Sci. USA* 76(12):6314–6318 (1979).

Van Beveren, C. et al., "RNA Tumor Viruses" *Molecular Biology of Tumor Viruses*, 2nd ed., vol. 2. Cold Spring Harbor Laboratory Press, pp. 773–779 (1985).

Zoller, M.J. and Smith, M., "Oligonucleotide–Directed Mutagenesis of DNA Fragments Cloned into M13 Vectors," *Methods in Enzymology* 100:468–500 (1983).

Brewer, L.C. and Wells, R.D., "Mechanistic Independent of Avian Myeloblastosis Virus DNA Polymerase and Ribonuclease H," *J. Virol.* 14:1494–1502 (1974).

Kimmel, A.R. and Berger, S.L., "Preparation of cDNA and the Generation of cDNA Libraries: Overview," *Meth. Enzymol.* 152:307–389 (1987).

Myers, J.C. and Spiegelman, S., "Sodium pyrophosphate inhibition of RNA•DNA hybrid degradation by reverse tanscriptase," *PNAS USA*:75:5329–5333 (1978).

Rho, H.M., "Biochemical and Immunological Characterization of the DNA Polymerase and RNase H in Feline Leukemia Virus," *Korean J. Zoology* 22:141–152 (1979).

Rho, H.M. and Gallo, R.C., "Biochemical and Immunological Properties of the DNA Polymerase and RNAase H Activities of Purified Feline Leukemia Virus Reverse Transcriptase," *Cancer Letters* 10:207–221 (1980).

Weiss, J. et al., "Production and Characterization of Monoclonal Antibodies Against Avian Retrovirus Reverse Transcriptase," *J. Virol.* 45:859–863 (1983).

Weiss, R. et al., eds., *Molecular Biology of Tumor Viruses*, 2d edition, Chapter 5, "RNA Tumor Viruses," pp. 75–80, Cold Spring Harbor Laboratory (1985).

Berger, S.L. et al., "Reverse Transcriptase and Its Associated Ribonuclease H: Interplay of Two Enzyme Activities Controls the Yield of Single–Stranded Complementary Deoxyribonucleic Acid," *Biochem.* 22:2365–2372 (1983).

Dudding, L.R. et al., "Analysis of the RNA– and DNA–Dependent DNA Polymerase Activities of Point Mutants of HIV–1 Reverse Transcriptase Lacking Ribonuclease H Activity," *Biochem.* 30:10498–10506 (Oct. 1991).

Gubler, U. and Hoffman, B.J., "A simple and very efficient method for generating cDNA libraries," *Gene* 25:263–269 (Nov. 1983).

Hizi, A. et al., "Mutational Analysis of the Ribonuclease H Activity of Human Immunodeficiency Virus 1 Reverse Transcriptase," *Virol.* 175:575–580 (Apr. 1990).

Houts, G.E. et al., "Reverse Transcriptase from Avian Myeloblastosis Virus," *J. Virol.* 29:517–522 (Feb. 1979).

Kanaya, S. et al., "Identification of the Amino Acid Residues Involved in an Active Site of *Escherichia coli* Ribonuclease H by Site–directed Mutagenesis," *J. Biol. Chem.* 265:4615–4621 (Mar. 1990).

Mizrahi, V. et al., "Site–directed mutagenesis of the conserved Asp–443 and Asp–498 carboxy–terminal residues of HIV–1 reverse transcriptase," *Nucl. Acids Res.* 18:5359–5363 (Sep. 1990).

Repaske, R. et al., "Inhibition of RNase H Activity and Viral Replication by Single Mutations in the 3' Region of Moloney Murine Leukemia Virus Reverse Transcriptase," *J. Virol.* 63:1460–1464 (Mar. 1989).

Schwartzberg, P. et al., "Construction and Analysis of Deletion Mutations, in the pol Gene of Moloney Murine Leukemia Virus: A New Viral Function Required for Productive Infection," *Cell* 37:1043–1052 (Jul. 1984).

Tanese N. and Goff, S.P., "Fine–Structure Mutational Analysis of the Reverse Transcriptase Domain of Moloney Murine Leukemia Virus," *RNA Tumor Viruses*, Cold Spring Harbor Laboratory, Cold Spring Harbor, New York (May 19–May 24, 1987).

Telesnitsky, A. and Goff, S.P., "RNase H domain mutations affect the interaction between Moloney murine leukemia virus reverse transcriptase and its primer–template," *Proc. Natl. Acad. Sci. USA* 90:1276–1280 (Feb. 1993).

"Defendant's Supplemental Response to Plaintiff's Interrogatory No. 13," dated May 15, 1998 from *Life Technologies, Inc. v. Clontech Laboratories, Inc.*, U.S. District Court for the District of Maryland, Civil Action No. AW 96–4080.

Letter dated Oct. 9, 1987 from John E. Donelson, Exec. Editor of Nucleic Acids Research, Exhibit LTX 6402 from *Life Technologies, Inc. v. Clontech Laboratories, Inc.*, U.S. Disrict Court for the District of Maryland, Civil Action No. AW 96–4080.

Referee's Report on Kotewicz' et al., "Isolation of cloned Moloney murine leukemia virus . . . ," Exhibit LTX 6403 from *Life Technologies. Inc. v. Clontech Laboratories, Inc.*, U.S. District Court for the District of Maryland, Civil Action No. AW 96–4080.

Referee's Report on Kotewicz' et al., "Isolation of cloned Moloney murine leukemia virus . . . ," Exhibit LTX 6404 from *Life Technologies, Inc. v. Clontech Laboratories, Inc.*, U.S. District Court for the District of Maryland, Civil Action No. AW 96–4080.

Letter dated Nov. 17, 1987, from Gary F. Gerard, PH.D., Director Enzymology, Nucleic Acids & Recombinant DNA, Molecular Biology R&D, of Bethesda Research Laboratories, Life Technologies, Inc., Exhibits LTX 6405 and LTX 6406 in *Life Technologies, Inc. v. Clontech Laboratories, Inc.*, U.S. District Court for the District of Maryland, Civil Action No. AW 96–4080.

"Approval of Scientific Publications" form, Michael L. Kotewicz, requestor, dated Jul. 24, 1987, with note attached, Exhibits LTX 6407 and LTX 6408 from *Life Technologies, Inc. v. Clontech Laboratories, Inc.*, U.S. District Court for the District of Maryland, Civil Action No. Aw 96–4080.

Memorandum from Dietmar Rabussay dated Aug. 18, 1987, Exhibits LTX 6409 and LTX 6410 from *Life Technologies, Inc. v. Clontech Laboratories, Inc.*, U.S. District Court for the District of Maryland, Civil Action No. AW 96–4080.

Defendant's "Answer" dated Jan. 24, 1995 from *Life Technologies, Inc. v. Promega Corporation*, U.S. District Court for the District of Maryland, Civil Action No. AW 94–2776.

"Consent Judgment" dated Mar. 31, 1995 from *Life Technologies, Inc. v. Promega Corporation*, U.S. District Court for the District of Maryland, Civil Action No. AW 94–2776.

Defendant's "Answer and Counterclaim" dated Feb. 6, 1995 from *Life Technologies, Inc. v. Strategene, Inc.*, U.S. District Court for the District of Maryland, Civil Action No. AW 94–2777.

"Memorandum Opinion" dated Jul. 27, 1995 from *Life Technologies, Inc. v. Stratagene, Inc.*, U.S. District Court for the District of Maryland, Civil Action No. AW 94–2777.

"Order" dated Jul. 27, 1995, from *Life Technologies, Inc. v. Strategene, Inc.*, U.S. District Court for the Disrict of Maryland, Civil Action No. AW 94–2777.

"Strategene's Responses and Objections to Plaintiff's Second Set of Interrogatories to Defendant and Second Request for Production of Documents and Things" dated Aug. 7, 1995, from *Life Technologies, Inc. v. Stratagene, Inc.*, U.S. District Court for the District of Maryland, Civil Action No. AW 94–2777, including (a) Weis, *J. Virol.* 45:859–863 (1983); (b) Rho & Gallo, *Cancer Letters* 10:207–221 (1980) and (c) Rho, *Korean Journal of Zoology* 22:141–152 (1970).

Defendant's "Amended Answer and Affirmative Defenses" dated Jul. 11, 1997 from *Life Technologies, Inc. v. Clontech Laboratories, Inc.*, U.S. District Court for the District of Maryland, Civil Action No. AW–96–4080.

"Life Technologies, Inc., Invention Disclosure Form" dated Apr. 30, 1987, Exhibit Nos. LTX32497–LTX32502, from *Life Technologies, Inc. v. Clontech Laboratories, Inc.*, U.S. District Court for the District of Maryland, Civil Action No. AW–96–4080.

Handwritten note by Brian Schmidt, employee of Life Technologies, Inc., Exhibit LTX35171 in *Life Technologies, Inc. v. Clontech Laboratories, Inc.*, U.S. District Court for the District of Maryland, Civil Action No. AW 96–4080.

"Complaint" dated Dec. 22, 1998, from *Clontech Laboratories, Inc. v. Life Technologies, Inc.*, U.S. District Court for the District of Delaware, Civil Action No. 98–750.

"Memorandum Opinion" and accompanying "Order" dated Feb. 18, 1999, from *Life Technologies, Inc. v. Clontech Laboratories, Inc.*, U.S. District Court for the District of Maryland, Southern Division, Civil Action No. AW–96–4080.

Amuro, N. et al., "Replacement by site–directed mutagenesis indicates a role for histidine 170 in the glutamine amide transfer function of anthranilate synthase," *J. Biol. Chem.* 260:14844–14849 (1985).

Bryant, D.L. et al., "Amino acid alterations within a highly conserved region of the Rous sarcoma virus src gene product pp60src inactivate tyrosine protein kinase activity," *Mol. Cell. Biol.* 4:862–866 (1984).

Gerard, G.F. et al., "cDNA synthesis by cloned Moloney murine leukemia virus reverse transcriptase lacking Rnase H activity," *Focus* 11:66–69 (1989).

Houdebine, L.–M., "Synthesis of DNA complementary to the mRNAs for milk proteins by *E. coli* DNA polymerase I," *Nuc. Acids Res.* 3:615–630 (1976).

Ivanoff, L.A. et al., "Expression and site–specific mutagenesis of the poliovirus 3C protease in *Escherichia coli*," *Proc. Natl. Acad. Sci. USA* 83:5392–5396 (1986).

Joyce, C.M. et al., "Construction of a plasmid that overproduces the large proteolytic fragment (Klenow fragment) of DNA polymerase I of *Escherichia coli*," *Proc. Natl. Acad. Sci. USA* 80:1830–1834 (1983).

Voordouw, G. et al., "Site–directed mutagenesis of the small subunit of ribulose–1,5–bisphosphte carboxylase/oxygenase from *Anacystis nidulans*," *Eur. J. Biochem.* 163:591–598 (1987).

Copeland, T.D. et al., "Amino– and Carboxyl–Terminal Sequence of Moloney Murine Leukemia Virus Reverse Transcriptase," *Virology* 143:676–679 (1985).

Crouch,R. and Dirksen, M.–L., "Ribonucleases H", in *Nucleases*, Linn, S. and Roberts, R., eds., Cold Spring Harbor Laboratory Press, Cold Spring Harbor, N.Y., pp 211–241 (1982).

Freeman–Wittig, M.–J. et al., "Diferential Effects of Captan on DNA Polymerase and Ribonuclease H Activities of Avian Myeloblastosis Virus Reverse Trancriptase," *Biochemistry* 25:3050–3055 (1986).

Freeman–Wittig, M.–J. et al., "Captan binding to avian myeloblastosis virus reverse transcriptase and its effect of RNase H activity," *Mol. Cell. Biochem.* 94:9–17 (1990).

Gerard, G., "Comparison of cDNA Synthesis by Avian and Cloned Murine Reverse Transcriptase," *Focus* 7:1–3 (1985).

Gerard, G. et al., "cDNA Synthesis by Moloney Murine Leukemia Virus RNase H–Minus Reverse Transcriptase Possessing Full DNA Polymerase Activity," *Focus* 14:91–93 (1994).

Goff, S.P., "Genetic and Biochemical Approach to the Study of Retroviral Replication", Abstract from the $7^{th}$ Annual DNA Congress, San Francisco, CA (Mar. 1987).

Grandgenett, D. et al., "Activiation of an $MG^{2+}$–Dependent DNA Endonuclease of Avian Myeloblastosis Virus αβ DNA Polymerase by In Vitro Proteolytic Cleavage," *J. Virology* 33:264–271 (1980).

Grandgenett, D. et al., "Structural Characterization of the Avian Retrovirus Reverse Transcriptase and Endonuclease Domains," *J. Biol. Chem.* 260:8243–8249 (1985).

Green, M. and Gerard, G., "RNA–Directed DNA Polymerase–Properties and Functions in Oncogenic RNA Viruses and Cells," *Progress in Nucleic Acid Research and Molecular Biology* 14:188–334 (1974).

Hansen, J. et al., "Identification and characterization of HIV–specific RNase H by monoclonal antibody," *EMBO J.* 7:239–243 (1988).

Hizi, A. et al., "Expression of soluble, enzymatically active, human immunodeficiency virus reverse transcriptase in *Escherichia coli* and analysis of mutants," *Proc. Natl. Acad. Sci. USA* 85:1218–1222 (1988).

Hizi, A. et al., "The Effects of Cysteine Mutations on Reverse Transcriptases of Human Immunodeficiency Virus Types 1 and 2," *J. Biol. Chem.* 267:1293–1297 (1992).

Holmes, M. H., "Elimination of Unwanted Restriction Sites from a Plasmid Bearing the Reverse Transcriptase Gene of Moloney Murine Leukemia Virus," University of Maryland, Baltimore County, MD, Oct. 6, 1986.

Hostomsky, S. et al., "Ribonucleases H," in *Nucleases*, $2^{nd}$ ed., Linn, S. and Roberts, R., eds. Cold Spring Harbor Laboratory Press, Cold Spring Harbor, NY, pp. 341–376 (1993).

Jacobsen, H. et al., "The N–Terminal Amino–Acid Sequences of DNA Polymerase I from *Escherichia coli* and of the Large and the Small Fragments Obtained by a Limited Proteolysis," *Eur. J. Biochem.* 45:623–627 (1974).

Katayanagi, K. et al., "Crystal Structures of Ribonuclease HI Active Site Mutants from *Escherichia coli*," *J. Biol. Chem.* 268:22092–22099 (1993).

Klenow, H. and Henningsen, "Selective Elimination of the Exonuclease Activity of the Deoxyribonucleic Acid Polymerase from *Escherichia coli* B by Limited Proteolysis," *Proc. Natl. Acad. Sci. USA*, 65:168–175 (1970).

Gerard, G., Inhibition of SUPERSCRIPT II Reverse Transcriptase by Common Laboratory Chemicals, Documents regarding CAT Transcription Detection and SuperScript RNase H Reverse Transriptase brochure, from *Life Technologies, Inc. v. Clonetech Laboratories, Inc.*, U.S. District Court for the District of Maryland Southern Division, Civil Action No. AW96–4080, LTX18287– LTX18318, and LTX18321–LTX18344.

Margalith, M. et al., "Differential inhibition of DNA polymerase and RNase H activities of the reverse transcriptase by phosphonoformate," *Mol. Cell. Biochem.* 43:97–103 (1982).

Mizrahi, V. et al., "Recombinant HIV–1 Reverse Transcriptase: Purification, Primary Structure, and Polymerase/Ribonuclease H Activities," *Arch. Biochem. Biophys.* 273:347–358 (1989).

Modak, M.J. and Marcus, S.L., "Purification and Properties of Rauscher Leukemia Virus DNA Polymerase and Selective Inhibiton of Mammalian Viral Reverse Transcriptase by Inorganic Phosphate," *J. Biol. Chem.* 252:11–19 (1977).

Nakamura, H. et al., "Structural models of ribonuclease H domains in reverse transcriptase from retroviruses," *Nucleic Acids Res.* 19:1817–1823 (1991).

Prasad, V. and Goff, S., "Linker insertion mutagenesis of the human immunodeficiency virus reverse transcriptase expressed in bacteria: Definition of the minimal polymerase domain," *Proc. Natl. Acad. Sci. USA* 86:3104–3108 (1989).

Roth, M. et al., "Purification and Characterization of Murine Retroviral reverse Transcriptase Expressed in *Escherichia coli*," *J. Biol. Chem.* 260:9326–9335 (1985).

Schatz, O. et al., "Point mutations in conserved amino acid residues within the C–terminal domain of HIV–1 reverse transcriptase specifically repress RNase H function," *FEBS Lett.* 257:311–314 (1989).

Schatz, O. et al., "Inactivation of the RNase H Domain of HIV–1 Reverse Transcriptase Blocks Viral Infectivity," *Adv. Appl. Biotech. Series* 7:293–303 (1989).

Skalka and Goff, S. eds., *Reverse Transcriptase*, Cold Spring Harbor Laboratory Press, Cold Spring Harbor, N.Y. (1993).

Tanese, M. and Goff, S., "Domain Structure of the Moloney Murine Leukemia Virus Reverse Transcriptase: Mutational Analysis and Separate Expression of the DNA Polymerase and RNase H Activities," *Proc. Natl. Acad. Sci. USA* 85:1777–1781 (1988).

Telesnitsky, A. et al., "Defects in Moloney Murine Leukemia Virus Replication Caused by a Reverse Transcriptase Mutation Modeled on the Structure of *Escherichia coli* RNase H," *J. Virology* 66:615–622 (1992).

Tisdale, M. et al., "Mutations within the RNAse H domain of human immunodeficiency virus type 1 reverse transcriptase abolish virus infectivity," *J. General Virology* 72:59–66 (1991).

Varmus, H. and Swanstrom, R., "Replication of Retroviruses," in *Molecular Biology of Tumor Viruses, RNA Tumor Viruses* $2^{nd}$ ed., Cold Spring Harbor Laboratory Press, Cold Spring harbor, N.Y., pp. 369–512 (1982).

Zhan,X. et al., "The Isolated RNase H Domain of Murine Luekemia Virus Reverse Transcriptase," *J. Biol. Chem.* 272:22023–22039 (1997).

"Defendant's Notice Pursuant to 35 U.S.C. §282," from *Life Technologies, Inc. v. Clonetech Laboratories, Inc.*, U.S. District Court for the District of Maryland Southern Division, Civil Action No. AW96–4080, pp. 1–8.

"Transcript of Motions Hearing Before the Honorable Alexander Wiliams, Jr., United States District Judge," dated Jul. 13, 1999, pp. 1–48 from *Life Technologies, Inc. v. Clontech Laboratories, Inc.*, U.S. District Court for the District of Maryland, Southern Division, Civil Action No. AW–96–4080.

"Transcript of Motions Hearing Before the Honorable Alexander Williams, Jr., United States District Judge" (Direct examination of Michael Leslie Kotewicz), dated Jul. 13, 1999, pp. 1–65, from *Life Technologies, Inc. v. Clontech Laboratories, Inc.*, U.S. District Court for the District of Maryland, Southern Division, Civil Action No. AW–96–4080.

"Morning Session" (Direct examination of Michael Leslie Kotewicz, cross examination of Michael Leslie Kotewicz, redirect examination of Michael Leslie Kotewicz, recross examination of Michael Leslie Kotewicz, direct examination of Robert Esmond), dated Jul. 14, 1999, pp. 66–163, from *Life Technologies, Inc. v. Clontech Laboratories, Inc.*, U.S. District Court for the District of Maryland, Southern Division, Civil Action No. AW–96–4080.

"Afternoon Session" (Direct examination of Robert Esmond, cross examination of Robert Esmond, direct examination of Harry F. Manbeck, cross examination of Harry F. Manbeck, redirect examination of Harry F. Manbeck, direct examination of Gary Floyd Gerard), dated Jul. 14, 1999, pp. 164–259, from *Life Technologies, Inc. v. Clontech Laboratories, Inc.*, U.S. District Court for the District of Maryland, Southern Division, Civil Action No. AW–96–4080.

"Morning Session" (Direct examination of Gary Floyd Gerard, cross examination of Gary Floyd Gerard, redirect examination of Gary Floyd Gerard, recross examination of Gary Floyd Gerard, direct examination of James J. Champoux, cross examination of James J. Champoux, redirect examination of James J. Champoux), dated Jul. 15, 1999, pp. 260–352, from *Life Technologies, Inc. v. Clontech Laboratories, Inc.*, U.S. District Court for the District of Maryland, Southern Division, Civil Action No. AW–96–4080.

"Transcript of Motions Hearing Before the Honorable Alexander Williams, Jr., United States District Judge" (Decision of the court), dated Jul. 16, 1999, pp. 423–451, from *Life Technologies, Inc. v. Clontech Laboratories, Inc.*, U.S. District Court for the District of Maryland, Southern Division, Civil Action No. AW–96–4080.

Garnier, J. et al., "Analysis of the Accuracy and Implications of Simple Methods for Predicting the Secondary Structure of Globular Proteins," *J. Mol. Biol.* 120:97–120 (1978).

Gerard, G.F., "Chapter 1. Reverse Transcriptase," in *Enzymes of Nucleic Acid Synthesis and Modification, vol. I, DNA Enzymes*, Jacob, S.T., ed., CRC Press, Inc., Boca Raton, FL, pp. 1–38 (1983).

Grandgenett, D.P. et al., "A Single Subunit form Avian Myeloblastosis Virus with Both RNA–Directed DNA Polymerase and Ribonuclease H Activity," *Proc. Natl. Acad. Sci. USA* 70:230–234 (1973).

Houts, G.E. et al., "Reverse Transcriptase from Avian Myelobastosis Virus," *J. Virol.* 29:517–522 (1979).

Kanaya, S. and R.J. Crouch, "Low Levels of RNase H Activity in *Escherichia coli* FB2 rnh Result from a Single–Base Change in the Structural Gene of RNase H," *J. Bacteriol.* 154:1021–1026 (1983).

Moelling, K., "Characterization of Reverse Transcriptase and RNase H from Friend–Murine Leukemia Virus," *Virology* 62:46–59 (1974).

Moelling, K., "Further Characterization of the Friend Murine Leukemia Virus Reverse Transriptase–RNase H Complex," *J. Virol.* 18:418–425 (1976).

Old, R.W. and S.B. Primrose, "Cloning cDNA by Homopolymer Tailing," in *Principles of Gene Manipulation, An Introduction to Genetic Engineering*, 2nd Ed., University of California Press, Los Angeles, CA, pp. 26–27 (1981).

Omer, C.A. and A.J. Fares, "Mechanism of Release of the Avian Retroviruses tRNA$^{Trp}$ Primer Molecule from Viral DNA by Ribonuclease H During Reverse Transcription," *Cell* 30:797–805 (1982).

Toh, H. et al., "Close structural resemblance between putative polymerse of a Drosophila transposable genetic element 17.6 and pol gene product of Moloney murine leukaemia virus," 4:1267–1272 (1985).

Varmus, H., "Mechanisms Involved in the Synthesis of Retroviral DNA," in *RNA Tumor Viruses*, Weiss, R. et al., eds., Cold Spring Harbor Laboratory, pp. 410–423 (1982).

Defendant's Exhibit No. 14, LTX32496—LTX32502, from *Life Technologies, Inc. v. Clontech Laboratories, Inc.*, U.S. District Court for the District of Maryland, Southern Division, Civil Action No. AW–96–4080.

Defendant's Exhibit No. 50, LTX34776—LTX34780, from *Life Technologies, Inc. v. Clontech Laboratories, Inc.*, U.S. District Court for the District of Maryland, Southern Division, Civil Action No. AW–96–4080.

Defendant's Exhibit No. 88, LTX277—LTX281, from *Life Technologies, Inc. v. Clontech Laboratories, Inc.*, U.S. District Court for the District of Maryland, Southern Division, Civil Action No. AW–96–4080.

Defendant's Exhibit No. 124, LTX35319—LTX35320, from *Life Technologies, Inc. v. Clontech Laboratories, Inc.*, U.S. District Court for the District of Maryland, Southern Division, Civil Action No. AW–96–4080.

Defendant's Exhibit No. 136, LTX35341—LTX35343, from *Life Technologies, Inc. v. Clontech Laboratories, Inc.*, U.S. District Court for the District of Maryland, Southern Division, Civil Action No. AW–96–4080.

Defendant's Exhibit No. 137, LTX35344—LTX35345, from *Life Technologies, Inc. v. Clontech Laboratories, Inc.*, U.S. District Court for the District of Maryland, Southern Division, Civil Action No. AW–96–4080.

Defendant's Exhibit No. 138, LTX35346—LTX35348, from *Life Technologies, Inc. v. Clontech Laboratories, Inc.*, U.S. District Court for the District of Maryland, Southern Division, Civil Action No. AW–96–4080.

Defendant's Exhibit No. 237, LTX6408, from *Life Technologies, Inc. v. Clontech Laboratories, Inc.*, U.S. District Court for the District of Maryland, Southern Division, Civil Action No. AW–96–4080.

Defendant's Exhibit No. 238, LTX6409—LTX6410, from *Life Technologies, Inc. v. Clontech Laboratories, Inc.*, U.S. District Court for the District of Maryland, Southern Division, Civil Action No. AW–96–4080.

Defendant's Exhibit No. 259, LTX34739—LTX34763, from *Life Technologies, Inc. v. Clontech Laboratories, Inc.*, U.S. District Court for the District of Maryland, Southern Division, Civil Action No. AW–96–4080.

Defendant's Exhibit No. 394, from *Life Technologies, Inc. v. Clontech Laboratories, Inc.*, U.S. District Court for the District of Maryland, Southern Division, Civil Action No. AW–96–4080.

Defendant's Exhibit No. 399, from *Life Technologies, Inc. v. Clontech Laboratories, Inc.*, U.S. District Court for the District of Maryland, Southern Division, Civil Action No. AW–96–4080.

Defendant's Exhibit No. 398, from *Life Technologies, Inc. v. Clontech Laboratories, Inc.*, U.S. District Court for the District of Maryland, Southern Division, Civil Action No. AW–96–4080.

Defendant's Exhibit No. 397, from *Life Technologies, Inc. v. Clontech Laboratories, Inc.*, U.S. District Court for the District of Maryland, Southern Division, Civil Action No. AW–96–4080.

Defendant's Exhibit No. 396, from *Life Technologies, Inc. v. Clontech Laboratories, Inc.*, U.S. District Court for the District of Maryland, Southern Division, Civil Action No. AW–96–4080.

Defendant's Exhibit No. 401, from *Life Technologies, Inc. v. Clontech Laboratories, Inc.*, U.S. District Court for the District of Maryland, Southern Division, Civil Action No. AW–96–4080.

Defendant's Exhibit No. 433, from *Life Technologies, Inc. v. Clontech Laboratories, Inc.*, U.S. District Court for the Disrict of Maryland, Southern Division, Civil Action No. AW–96–4080.

"Subpoena in a Civil Case" dated Aug. 21, 1997, served upon Stephen P. Goff, *Life Technologies, Inc. v. Clontech Laboratories, Inc.*, Civil Action No. AW 96–4080, U.S. District Court for the District of Maryland, Southern Division.

"Stipulation and Protective Order Re Confidential Documents of Non–Parties Columbia University and Dr. Stephen P. Goff," *Life Technologies, Inc. v. Clontech Laboratories, Inc.*, Civil Action No. AW 96–4080, U.S. District Court for the District of Maryland, Southern Division.

Letter from ATCC to Robert W. Esmond dated Dec. 10, 1999.

Buiser, R.G. et al., "Requirements for the catalysis of strand transfer synthesis by retroviral DNA polymerases," *J. Biol. Chem.* 266:13103–13109 (1991).

DeStefano, J.J. et al., "Polymerization and Rnase H activities of the reverse transcriptases from avian myeloblastosis, human immunodeficiency, and Moloney murine leukema viruses," *J. Biol. Chem.* 266:7423–7431 (1991).

Goff,, S.P., and Lebel, L.I., "Mutants of murine leukemia viruses and retroviral replication," *Biochim. Biophys. Acta* 907:93–123 (1987).

*Life Technologies, Inc. v. Clontech Laboratories, Inc.*, Appeal 99–1550 (Fed. Cir. Sep. 21, 2000).

"Complaint for Declaratory Judgment," dated Jun. 22, 2000, from *Clontech Laboratories, Inc. v. Life Technologies, Inc.*, U.S. District Court, Southern District of Maryland, Civil Action No. AW 00 CV 1879.

Barr, P.J., et al., "Expression of Active Human Immunodeficiency Virus Reverse Transcriptase in *Saccharomyces Cerevisiae*," *Bio/Technology* 5:486–489, Nature Publishing Company (May 1987).

Bathurst, I.C., et al., "Characterization of the Human Immunodeficiency Virus Type–1 Reverse Transcriptase Enzyme Produced in Yeast," *Biochem. Biophys. Res. Commun.* 171:589–595, Academic Press, Inc. (1990).

Champoux, J.J., "Roles of Ribonuclease H in Reverse Transcription," in *Reverse Transcriptase*, Ch. 6, Cold Spring Harbor Laboratory Press, Cold Spring Harbor, New York, pp. 103–117 (1993).

Farmerie, W.G., et al., "Expression and Processing of the AIDS Virus Reverse Transcriptase in *Escherichia coli*," *Science* 236:305–308, Association for the Advancement of Science (1987).

Georgiadis, M., et al., "Mechanistic implications from the structure of a catalytic fragment of Moloney murine leukemia virus reverse transcriptase," *Structure* 3:879–892, Current Biology LTD., (1995).

Golomb, M. and Grandgenett, D.P., "Endonuclease Activity of Purified RNA–directed DNA Polymerase from Avian Myeloblastosis Virus," *J. Biol. Chem.* 254:1606–1613, American Society of Biological Chemists, Inc., (1979).

Hansen, J., et al., "RNase H Activity Associated with Bacterially Expressed Reverse Transcriptase of Human T–cell Lymphotropic Virus III/Lymphadenopathy–associated Virus," *J. Biol. Chem.* 262:12393–12396, American Society for Biochemistry and Molecular Biology, (1987).

Hansen, J., et al., "Identification and characterization of HIV–specific RNase H by monoclonal antibody," *EMBO J.* 7:239–243, IRL Press Limited (1988).

Houts, G.E., et al., "Reverse Transcriptase from Avian Myeloblastosis Virus," *J. Virol.* 29:517–522, American Society for Microbiology (1979).

Huber, H.E., et al., "Human Immunodeficiency Virus 1 Reverse Transcriptase," *J. Biol. Chem.* 264:4669–4678, American Society for Biochemistry and Molecular Biology, Inc. (1989).

Inouye, S., and Inouye, M., "Bacterial Reverse Transcriptase," in *Reverse Transcriptase*, Ch. 17, Cold Spring Harbor Laboratory Press, Cold Spring Harbor, New York, pp. 391–410 (1993).

Kacian, D.L. and Myers, J.C., "Synthesis of extensive, possibly complete, DNA copies of poliovirus RNA in high yields and at high specific activities," *Proc. Natl. Acad. Sci. USA* 73:2191–2195, National Academy of Sciences USA (1976).

Larder, B., et al., "Site–Specific mutagenesis of AIDS virus reverse transcriptase," *Nature* 327:716–717, Macmillan Publishers Ltd. (1987).

Larder, B., et al., "AIDS virus reverse transcriptase defined by high level expression in *Escherichia coli*," *EMBO J.* 6:3133–3137, IRL Press Limited (1987).

Le Grice, S., "Human Immunodeficiency Virus Reverse Transcriptase," in *Reverse Transcriptase*, Skalla, A.M. and Goff, S.P., eds., Cold Spring Harbor Laboratory Press, Cold Spring Harbor, New York, pp. 163–191 (1993).

Levin, J.G., et al., "Functional Organization of the Murine Leukemia Virus Reverse Transcriptase: Characterization of a Bacterially Expressed AKR DNA Polymerase Deficient in RNASE H Activity," *J. Virol.* 62:4376–4380, American Society for Microbiology (1988).

Lightfoote, M.M., et al., "Structural Characterization of Reverse Transcriptase and Endonuclease Polypeptides of the Acquired Immunodeficiency Syndrome Retrovirus," *J. Virol.* 60:771–775, American Society for Microbiology (1986).

Lori, F., et al., "Enzymatically Active Forms of Reverse Transcriptase of the Human Immunodeficiency Virus," *AIDS Res. Hum. Retroviruses* 4:393–398, Mary Ann Leibert, Inc., Publishers (1988).

Lowe, D.M., et al., "HIV–1 Reverse Transcriptase: Crystallization and Analysis of Domain Structure by Limited Proteolysis," *Biochemistry* 27:8884–8889, American Chemical Society (1988).

Mizrahi, V., et al., "Mutagenesis of the Conserved Aspartic Acid 443, Glutamic Acid 478, Asparagine 494, and Aspartic Acid 498 Residues in the Ribonuclease H Domain of p66/p51 Human Immunodeficiency Virus Type 1 Reverse Transcriptase," *J. Biol. Chem.* 269:19245–19249, American Society for Biochemistry and Molecular Biology, Inc. (1994).

Müller, B., et al., "Co–expression of the Subunits of the Heterodimer of HIV–1 Reverse Transcriptase in *Escherichia coli*," *J. Biol. Chem.* 264:13975–13978, American Society for Biochemistry and Molecular Biology, Inc. (1989).

Myers, J.C., et al., "Synthesis of full–length DNA copies of avian meyloblastosis virus RNA in high yields," *Proc. Natl. Acad. Sci. USA* 74:2840–2843, National Academy of Sciences USA (1977).

Myers, J.C., et al., RNA primer used in synthesis of anticomplementary DNA by reverse transcriptase of avian myeloblastosis virus, *Proc. Natl. Acad. Sci. USA* 77:1316–1320, National Academy of Sciences USA (1980).

Najmudin, S., et al., "Crystal Structures of an N–terminal Fragment from Moloney Murine Leukemia Virus Reverse Transcriptase Complexed with Nucleic Acid: Functional Implications for Template–primer Binding to the Fingers Domain," *J. Mol. Biol.* 296:613–632, Academic Press, Inc. (2000).

Prasad, V.R., "Genetic Analysis of Retroviral Reverse Transcriptase Structure and Function," in *Reverse Transcriptase*, Skalla, A.M. and Goff, S.P., eds., Cold Spring Harbor Laboratory Press, Cold Spring Harbor, New York, pp. 135–162 (1993).

Reardon, J., et al., "Human Immunodeficiency Virus Reverse Transcriptase," *J. Biol. Chem.* 266:14128–14134, American Society for Biochemistry and Molecular Biology, Inc. (1991).

Schatz, O., et al., "HIV–1 RT–associated ribonuclease H displays both endonuclease and 3' → 5' exonuclease activity," *EMBO J.* 9:1171–1176, IRL Press Limited (1990).

Schiff, R.D. and Grandgenett, D.P., "Virus–Coded Origin of a 32,000–Dalton Protein from Avian Retrovirus Cores: Structural Relatedness of p32 and the β Polypeptide of the Avian Retrovirus DNA Polymerase," *J. Virol.* 28:279–291, American Society for Microbiology (1978).

Skalka, A.M., "Endonuclease Activity Associated with Reverse Transcriptase of Avian Sarcoma–Leukosis Viruses," in *Reverse Transcriptase*, Ch. 10, Cold Spring Harbor Laboratory Press, Cold Spring Harbor, New York, pp. 193–204 (1993).

Srivastava, A. and Modak, M.J., "Reverse Transcriptase–Associated RNASE H. Part IV. Pyrophosphate does not inhibit RNASE activity of AMV DNA polymerase," *Biochem. Biophys. Res. Commun.* 91:892–899, Academic Press, Inc. (1979).

Starnes, M.C., et al., "Enzyme Activity Gel Analysis of Human Immunodeficiency Virus Reverse Transcriptase," *J. Biol. Chem.* 263:5132–5134, American Society for Biochemistry and Molecular Biology, Inc. (1988).

Takatsuji, H., et al., "Expression of cauliflower mosaic virus reverse transcriptase in yeast," *Nature* 319:240–243, Macmillan Publishers Ltd. (1986).

Tanese, N., et al., "Expression of Reverse Transcriptase Activity of Human T–Lymphotropic Virus Type III (HTLV–III/LAV) in *Escherichia coli*," *J. Virol.* 59:743–745, American Society for Microbiology (1986).

Thimmig, R.L. and McHenry, C.S., "Human Immunodeficiency Virus Reverse Transcriptase," *J. Biol. Chem.* 268:16528–16536, American Society for Biochemistry and Molecular Biology, Inc. (1993).

Tisdale, M., et al., "Characterization of Human Immunodeficiency Virus Type 1 Reverse Transcriptase by Using Monoclonal Antibodies: Role of the C Terminus in Antibody Reactivity and Enzyme Function," *J. Virol.* 62:3662–3667, American Society for Microbiology (1988).

Tisdale, M., et al., "Structural characterization of HIV reverse transcriptase: A target for the design of specific virus inhibitors," *J. Antimicrobiol. Chemother.* 23(*Suppl A*):47–54, Academic Press, Inc. (1989).

Van Beveren, C. and Goulian, M., "Optimal Conditions for Synthesis of Long Complementary DNA Product with Moloney Murine Leukemia Virus," *J. Viol.* 30:951–954, American Society for Microbiology (1979).

Veronese, F., et al., "Characterization of Highly Immunogenic p66/p51 as the Reverse Transcriptase of HTLV–III/LAV," *Science* 231:1289–1291, Association for the Advancement of Science (1986).

Volkmann, S., et al., "Enzymatic Analysis of Two HIV–1 Reverse Transcriptase Mutants with Mutations in Carboxyl–terminal Amino Acid Residues Conserved among Retroviral Ribonucleases H," *J. Biol. Chem.* 268:2674–2683, American Society for Biochemistry and Molecular Biology, Inc. (1993).

Wöhrl, B.M., et al., "Kinetic Analysis of Four HIV–1 Reverse Transcriptase Enzymes Mutated in the Primer Grip Region of p66," *J. Biol. Chem.* 272:17581–17587, American Society for Biochemistry and Molecular Biology, Inc. (1997).

"Complaint," dated Jun. 29, 2000, from *Life Technologies, Inc. v. Promega Corporation*, U.S. District Court, Western District of Wisconsin, Civil Action No. 00C 0407 C.

"Answer," dated Oct. 17, 2000, from *Life Technologies, Inc. v. Promega Corporation*, U.S. District Court, Western District of Wisconsin, Civil Case No. 00–C–0407–C.

"Complaint," dated Jun. 29, 2000, from *Life Technologies, Inc. v. Stratagene Holding Corp., Stratagene, Inc., and Biocrest Manufacturing, L.P.*, U.S. District Court, District of Delaware, Civil Action No. 00–620.

"Answer," dated Nov. 30, 2000, from *Life Technologies, Inc. v. Stratagene Holding Corp., Stratagene, Inc., and Biocrest Manufacturing, L.P.*, U.S. District Court, District of Delaware, Civil Action No. 00–620.

Chattopadhyay, D., et al., "Resolution of Microheterogeneity Associated with Recombinant HIV–1 Heterodimeric Reverse Transcriptase," *Protein Expression and Purification* 3:151–159, Academic Press, Inc. (1992).

Gerard, G.F., "Synthesis of High Specific Activity cDNA," *Focus* 10:12–13, Life Technologies, Inc. (1988).

Hizi, A. and Joklik, W.K., "RNA–dependent DNA Polymerase of Avian Sarcoma Virus B77," *J. Biol. Chem.* 252:2281–2289, The American Society of Biological Chemists, Inc. (1977).

Myers, J.C. and Spiegelman, S., "Sodium pyrophosphate inhibition of RNA•DNA hybrid degradation by reverse transcriptase," *Proc. Natl. Acad. Sci. USA* 75:5329–5333, Proceedings of the National Academy of Sciences (1978).

Verma, I.M., "Studies on Reverse Transcriptase of RNA Tumor Viruses. III. Properties of Purified Moloney Murine Leukemia Virus DNA Polymerase and Associated RNase H," *J. Virol.* 15:843–854, American Society for Microbiology (1975).

Wang, L.–H. and Duesberg, P.H., "DNA Polymerase of Murine Sarcoma–Leukemia Virus: Lack of Detectable RNAse H and Low Activity With Viral RNA and Natural DNA Templates," *J. Virol.* 12:1512–1521, American Society for Microbiology (1973).

Allain, B. et al., "CIS Elements and Trans–acting Factors required for Minus Strand DNA Transfer during Reverse Transcription of the Genomic RNA of Murine Leukemia Virus," *J. Mol. Biol.* 277:225–235, Academic Press Limited (Mar. 1998).

Arendes, J. et al., "A Mutation in the rnh–locus of *Escherichia coli* Affects the Structural Gene for RNase H," *J. Biol. Chem.* 257:4719–4722, The American Society of Biological Chemists, Inc. (1982).

Arion, D. et al., "The K65R Mutation Confers Increased DNA Polymerase Processivity to HIV–1 Reverse Transcriptase," *J. Biol. Chem.* 271:19860–19864, The American Society for Biochemistry and Molecular Biology, Inc. (1996).

Arnold, E. et al., "Structure of HIV–1 reverse transcriptase/DNA complex at 7 Å resolution showing active site locations," *Nature* 357:85–89, Macmillan Publishers Ltd. (1992).

Bahar, I., "Collective Motions in HIV–1 Reverse Transcriptase: Examination of Flexibility and Enzyme Function," *J. Mol. Biol.* 285:1023–1037, Academic Press (Jan. 1999).

Basu, S. et al., "Sulphydryl groups in the template–primer–binding domain of murine leukaemia virus reverse transcriptase," *Biochem. J.* 296:577–583, The Biochemical Society (1993).

Beard, W.A. et al., "Structure/Function Studies of Human Immunodeficiency Virus Type 1 Reverse Transcriptase," *J. Biol. Chem.* 269:28091–28097, American Society for Biochemistry and Molecular Biology (1994).

Ben–Artzi, H. et al., "Characterization of the double stranded RNA dependent RNAse activity associated with recombinant reverse transcriptases," *Nucl. Acids Res.* 20:5115–5118, Oxford Unversity Press (1992).

Blain, S.W. and Goff, S.P., "Effects on DNA Synthesis and Translocation Caused by Mutations in the RNase H Domain of Moloney Murine Leukemia Virus Reverse Transcriptase," *J. Virol.* 69:4440–4452, American Society for Microbiology (1995).

Blain, S.W. and Goff, S.P., "Differential Effects of Moloney Murine Leukemia Virus Reverse Transcriptase Mutations on RNase H Activity in $Mg^{2+}$ and $Mn^{2+}$," *J. Biol. Chem.* 271:1448–1454, The American Society for Biochemistry and Molecular Biology, Inc. (1996).

Caliendo, A.M. et al., "Effects of Zidovudine–Selected Human Immunodeficiency Virus Type 1 Reverse Transcriptase Amino Acid Substitutions on Processive DNA Synthesis and Viral Replication," *J. Virol.* 70:2146–2153, American Society for Microbiology (1996).

Carl, P.L. et al., "Isolation and Mapping of a Mutation in *Escherichia coli* with Altered Levels of Ribonuclease H," *J. Bacteriol.* 144:28–35, American Society for Microbiology (1980).

Carmichael, G.G. and McMaster, G.K., "The Analysis of Nucleic Acids in Gels Using Glyoxal and Acridine Orange," *Meth. Enzymol.* 65:380–391, Academic Press, Inc. (1980).

Catucci, M. et al., "Development and Significance of the HIV–1 Reverse Transcriptase M184V Mutation During Combination Therapy With Lamivudine, Zidovudine, and Protease Inhibitors," *J. Acquir. Immune Defic. Syndr.* 21:203–208, Lippincott Williams & Wilkins, Inc. (Jul. 1999).

Chen, Y. and Marion, P.L., "Amino Acids Essential for RNase H Activity of Hepadnaivruses Are Also Required for Efficient Elongation of Minus–Strand Viral DNA," *J. Virol.* 70:6151–6156, American Society for Microbiology (1996).

Chowdhury, K. et al., "Elucidation of the Role of Arg 110 of Murine Leukemia Virus Reverse Transcriptase in the Catalytic Mechanism: Biochemical Characterization of Its Mutant Enzymes," *Biochemistry* 35:16610–16620, American Chemical Society (1996).

DeStefano, J.J. et al., "Requirements for Strand Transfer between Internal Regions of Heteropolymer Templates by Human Immunodeficiency Virus Reverse Transcriptase," *J. Virol.* 66:6370–6378, American Society for Microbiology (1992).

Diaz, L. and DeStefano, J.J., "Strand transfer is enhanced by mismatched nucleotides at the 3' primer terminus: a possible link between HIV reverse transcriptase fidelity and recombination," *Nucl. Acids Res.* 24:3086–3092, Oxford University Press (1996).

Ditta, G. et al., "Broad host range DNA cloning system for gram–negative bacteria: Construction of a gene bank of *Rhizobium meliloti*," *Proc. Natl. Acad. Sci (USA)* 77:7347–7351, National Academy of Sciences (1980).

Drosopoulos, W.C. and Prasad, V.R., "Increased Polymerase Fidelity of E89G, a Nucleoside Analog–Resistant Variant of Human Immunodeficiency Virus Type 1 Reverse Transcriptase," *J. Virol.* 70:4834–4838, American Society for Microbiology (1996).

Feng, J.Y. and Anderson, K.S., "Mechanistic Studies Examining the Efficiency and Fidelity of DNA Synthesis by the 3TC–Resistant Mutant (184V) of HIV–1 Reverse Transcriptase," *Biochemistry* 38:9440–9448, American Chemical Society (Jul. 1999; published on the web Jun. 30, 1999).

Fontaine, E. et al., "Fast Genotypic Detection of Drug Resistance Mutations in the HIV–1 Reverse Transcriptase Gene of Treatment–Naive Patients," *J. Hum. Virol.* 1:451–456, Lippincott Williams & Wilkins (Nov.–Dec. 1998).

Gao, G. et al., "Conferring RNA polymerase Activity to a DNA polymerase: A single residue in reverse transcriptase controls substrate selection," *Proc. Natl. Acad. Sci (USA)* 94:407–411, National Academy of Sciences (Jan. 1997).

Gao, G. and Goff, S.P., "Replication Defect of Moloney Murine Leukemia Virus with a Mutant Reverse Transcriptase That Can Incorporate Ribonucleotides and Deoxyribonucleotides," *J. Virol.* 72:5905–5911, American Society for Microbiology (Jul. 1998).

Gao, H.–Q. et al., "Similarities and Differences in the RNase H Activities of Human Immunodeficiency Virus Type 1 Reverse Transcriptase and Moloney Murine Leukemia Virus Reverse Transcriptase," *J. Mol. Biol.* 294:1097–1113 (Dec. 1999).

Georgiadis, M.M. et al., "Mechanistic implications from the structure of a catalytic fragment of Moloney murine leukemia virus reverse transcriptase," *Structure* 3:879–892, Current Biology Ltd. (1995).

Gerard, G.F., "Multiple RNase H Activities in Mammalian Type C Retravirus Lysates," *J. Virol.* 26:16–28, American Society Microbiology (1978).

Gerard, G.F. and D'Alessio, J.M., "Reverse Transcriptase (EC 2.7.7.49): The Use of Cloned Moloney Murine Leukemia Virus Reverse Transcriptase to Synthesize DNA from RNA," in *Methods in Molecular Biology, vol. 16: Enzymes of Molecular Biology*, Burrell, M.M., ed., Humana Press Inc., Totowa, N.J., pp. 73–93 (1993).

Goedken, E.R. and Marqusee, S., "Folding the Ribonuclease H Domain of Moloney Murine Leukemia Virus Reverse Transcriptase Requires Metal Binding or a Short N–Terminal Extension," *Proteins: Structure, Function, and Genetics* 33:135–143, Wiley–Liss, Inc. (Oct. 1998).

Goff, S. et al., "Isolation and Properties of Moloney Murine Leukemia Virus Mutants: Use of a Rapid Assay for Release of Virion Reverse Transcriptase," *J. Virol.* 38:239–248, American Society for Microbiology (1981).

Goff, S.P., "Retroviral Reverse Transcriptase: Synthesis, Structure, and Function," *J. Acquired Immune Deficiency Syndromes* 3:817–831, Raven Press, Ltd. (1990).

Goobar–Larsson, L. et al., "Disruption of a Salt Bridge between Asp 488 and Lys 465 in HIV–1 Reverse Transcriptase Alters Its Proteolytic Processing and Polymerase Activity," *Virology* 196:731–738, Academic Press, Inc. (1993).

Gopalakrishnan, V. et al., "Human immunodeficiency virus type 1 reverse transcriptase: Spatial and temporal relationship between the polymerase and RNase H activities," *Proc. Natl. Acad. Sci. (USA)* 89:10763–10767, National Academy of Sciences (1992).

Götte, M. et al., "The M184V Mutation in the Reverse Transcriptase of Human Immunodeficiency Virus Type 1 Impairs Rescue of Chain–Terminated DNA Synthesis," *J. Virol.* 74:3579–3585, American Society for Microbiology (Apr. 2000).

Gottesman, M.E. et al., "Transcription Antitermination by Bacteriophage Lambda N Gene Product," *J. Mol. Biol.* 140:57–75, Academic Press Inc. (1980).

Guo, J. et al., "Defects in Primer–Template Binding, Processive DNA Synthesis, and RNase H Activity Associated with Chimeric Reverse Transcriptases Having the Murine Leukemia Virus Polymerase Domain Joined to *Escherichia coli* RNase H," *Biochemistry* 34:5018–5029, American Chemical Society (1995).

Gutiérrez–Rivas, M. et al., "Mutational Analysis of Phe160 within the "Palm" Subdomain of Human Immunodeficiency Virus Type 1 Reverse Transcriptase," *J. Mol. Biol.* 290:615–625, Academic Press (Jul. 1999).

Hafkemeyer, P. et al., "HP 0.35, a cephalosporin degradation product is a specific inhibitor of lentiviral RNAses H," *Nucl. Acids Res.* 19:4059–4065, Oxford University Press (1991).

Han, L.–Y. et al., "Ribonuclease H Renaturation Gel Assay Using a Fluorescent–Labeled Substrate," *BioTechniques* 23:920–926, Eaton Publishing Co. (Nov. 1997).

Jacobo–Molina, A. et al., "Crystal structure of human immunodeficiency virus type 1 reverse transcriptase complexed with double–stranded DNA at 3.0 Å resolution shows bent DNA," *Proc. Natl. Acad. Sci. (USA)* 90:6320–6324, National Academy of Sciences (1993).

Jaeger, J. et al., "The structure of HIV–1 reverse transcriptase complexed with an RNA pseudoknot inhibitor," *EMBO J.* 17:4535–4542, Oxford University Press (Aug. 1998).

Jin, J. et al., "Analysis of the Role of Glutamine 190 in the Catalytic Mechanism of Murine Leukemia Virus Reverse Transcriptase," *J. Biol. Chem.* 274:20861–20868, The American Society for Biochemistry and Molecular Biology, Inc. (Jul. 1999).

Kanaya, S. and Crouch, R.J., "DNA Sequence of the Gene Coding for *Escherichia coli* Ribonuclease H," *J. Biol. Chem.* 258:1276–1281, The American Society of Biological Chemists, Inc. (1983).

Kanaya, S. and Crouch, R.J., "Low Levels of RNase H Activity in *Escherichia coli* FB2 rnh Result from a Single–Base Change in the Structural Gene of RNase H," *J. Bacteriol.* 154:1021–1026, American Society for Microbiology (1983).

Kanaya, S. and Crouch, R.J., "The rnh gene is essential for growth of *Escherichia coli*," *Proc. Natl. Acad. Sci. (USA)* 81:3447–3451, National Academy of Sciences (1984).

Kaushik, N. et al., "Tyrosine 222, a Member of the YXDD Motif of MuLV RT, Is Catalytically Essential and Is a Major Component of the Fidelity Center," *Biochemistry* 38:2617–2627, American Chemical Society (Mar. 1999; published on the web Feb. 10, 1999).

Kaushik, N. et al., "Role of Glutamine 151 of Human Immunodeficiency Virus Type–1 Reverse Transcriptase in Substrate Selection As Assessed by Site–Directed Mutagenesis," *Biochemistry* 39:2912–2920, American Chemical Society (Mar. 2000; published on the web Feb. 22, 2000).

Keck, J.L., et al., "Activation/Attenuation Model for RNase H. A One–Metal Mechanism with Second–Metal Inhibition," *J. Biol. Chem.* 273:34128–34133, The American Society for Biochemistry and Molecular Biology, Inc. (Dec. 1998).

Kelleher, C.D. and Champoux, J.J., "Characterization of RNA Strand Displacement Synthesis by Moloney Murine Leukemia Virus Reverse Transcriptase," *J. Biol. Chem.* 273:9976–9986, The American Society for Biochemistry and Molecular Biology, Inc. (Apr. 1998).

Kern, G. et al., "Characterization of a folding intermediate from HIV–1 ribonuclease H," *Protein Sci.* 7:2164–2174, Cambridge University Press (Oct. 1998).

Kohlstaedt, L.A. et al., "Crystal Structure at 3.5 Å Resolution of HIV–1 Reverse Transcriptase Complexed with an Inhibitor," *Science* 256:1783–1790, American Association for the Advancement of Science (1992).

Laemmli, U.K., "Cleavage of Structural Proteins during the Assembly of the Head of Bacteriophage T4," *Nature* 227:680–685, Macmillan (Journals) Limited (1970).

Larder, B.A. et al., "A Family of Insertion Mutations between Codons 67 and 70 of Human Immunodeficiency Virus Type 1 Reverse Transcriptase Confer Multinucleoside Analog Resistance," *Antimicrob. Agents Chemother.* 43:1961–1967, American Society for Microbiology (Aug. 1999).

Lavignon, M. et al., "Inhibition of Moloney Murine Leukemia Virus Reverse Transcriptse by α–Anomeric Oligonucleotides," *Biochem. Biophys. Res. Commun.* 161:1184–1190, Academic Press, Inc. (1989).

Levin, H.L., "An Unusual Mechanism of Self–Primed Reverse Transcription Requires the RNase H Domain of Reverse Transcriptase To Cleave an RNA Duplex," *Mol. Cell. Biol.* 16:5645–5654, American Society for Microbiology (1996).

Levin, H.L., "It's Prime Time for Reverse Transcriptase," *Cell* 88:5–8, Cell Press (Jan. 1997).

Loya, S. and Hizi, A., "The Interaction of Illimaquinone, a Selective Inhibitor of the RNase H Activity, with the Reverse Transcriptases of Human Immunodeficiency and Murine Leukemia Retroviruses," *J. Biol. Chem.* 268:9323–9328, The American Society for Biochemistry and Molecular Biology, Inc. (1993).

Madrid, M. et al., "Major Subdomain Rearrangement in HIV–1 Reverse Transcriptase Simulated by Molecular Dynamics," *Proteins: Structure, Function, and Genetics* 35:332–337, Wiley–Liss, Inc. (May 1999).

Maxam, A.M. and Gilbert, W., "Sequencing End–Labeled DNA with Base–Specific Chemical Cleavages," *Meth. Enzymol.* 65:499–560, Academic Press, Inc. (1980).

McDonell, M.W. et al., "Analysis of Restriction Fragments of T7 DNA and Determination of Molecular Weights by Electrophoresis in Neutral and Alkaline Gels," *J. Mol. Biol.* 110:119–146, Academic Press, Inc. (1977).

Medrano, L. et al., "Sequence Analysis of the Polymerase Domain of HIV–1 Reverse Transcriptase in Naive and Zidovudine–Treated Individuals Reveals a Higher Polymorphism in α–Helices as Compared with β–strands," *Virus Genes* 18:203–210, Kluwer Academic Publishers (Jun. 1999).

Messing, J., "New M13 Vectors for Cloning," *Meth. Enzymol.* 101:20–78, Academic Press, Inc. (1983).

Misra, H.S. et al., "An Enzymatically Active Chimeric HIV–1 Reverse Transcriptase (RT) with the RNase–H Domain of Murine Leukemia Virus RT Exists as a Monomer," *J. Biol. Chem.* 273:9785–9789, The American Society for Biochemistry and Molecular Biology, Inc. (Apr. 1998).

Murante, R.S. et al., "Junction ribonuclease: An activity in Okazaki fragment processing," *Proc. Natl. Acad. Sci. (USA)* 95:2244–2249, The National Academy of Sciences (Mar. 1998).

Nakamura, H. et al., "How does RNase H recognize a DNA–RNA hybrid?" *Proc. Natl. Acad. Sci. (USA)* 88:11535–11539, The National Academy of Sciences (1991).

Nishitani, H. et al., "Specific chromosomal sites enhancing homologous recombination in *Escherichia coli* mutants defective in RNase H," *Mol. Gen. Genet.* 240:307–314, Springer–Verlag (1993).

Olivares, I. et al., "Second–Site Reversion of a Human Immunodeficiency Virus Type 1 Reverse Transcriptase Mutant That Restores Enzyme Function and Replication Capacity," *J. Virol.* 73:6293–6298, American Society for Microbiology (Aug. 1999).

Patel, P.H. et al., "Insights into DNA Polymerization Mechanisms from Structure and Function Analysis of HIV–1 Reverse Transcriptase," *Biochemistry* 34:5351–5363, American Chemical Society (1995).

Peliska, J.A. and Benkovic, S.J., "Mechanism of DNA Strand Transfer Reactions Catalyzed by HIV–1 Reverse Transcriptase," *Science* 258:1112–1118, American Association for the Advancement of Science (1992).

Post, K. et al., "A Large Deletion in the Connection Subdomain of Murine Leukemia Virus Reverse Transcriptase or Replaement of the RNase H Domain with *Escherichia coli* RNase H Results in Altered Polymerase and RNase H Activities," *Biochemistry* 32:5508–5517, American Chemical Society (1993).

Precios, H.M. et al., "Multiple sites in HIV–1 reverse transcriptase associated with virological response to combination therapy," *AIDS* 14:31–36, Lippincott Williams & Wilkins (Jan. 2000).

Richardson, C.C. et al., "Enzymatic Synthesis of Deoxyribonucleic Acid," *J. Biol. Chem.* 239:222–231, The American Society of Biological Chemists, Inc. (1964).

Rodgers, D.W. et al., "The structure of unliganded reverse transcriptase from the human immunodeficiency virus type 1," *Proc. Natl. Acad. Sci. (USA)* 92:1222–1226, The National Academy of Sciences (1985).

Sarafianos, S.G. et al., "Crystal structure of HIV–1 reverse transriptase in complex with a polypurine tract RNA:DNA," *EMBO J.* 20:1449–1461, European Molecular Biology Organization (Mar. 2001).

Schultz, S.J. et al., "Polypurine Tract Primer Generation and Utilization by Moloney Murine Leukemia Virus Reverse Transcriptase," *J. Biol. Chem.* 274:34547–34555, The American Society for Biochemistry and Molecular Biology, Inc. (Dec. 1999).

Shirasawa, Y. et al., "Transdominant Inhibition of Moloney Murine Leukemia Virus Proliferation by Defective Mutants of Reverse Transcriptase," *J. Biochem.* 119:1070–1075, The Japanese Biochemical Society (1996).

Smith, C.M. et al, "Sequence Reuirements for Removal of tRNA by an Isolated Human Immunodeficiency Virus Type 1 RNase H Domain," *J. Virol.*72:6805–6812, American Society for Microbiology (Aug. 1998).

Smith, R.A. et al., "A New Point Mutation (P157S) in the Reverse Transcriptase of Human Immunodeficiency Virus Type 1 Confers Low–Level Resistance to (–)–β–2', 3'–Dideoxy–3'–Thiacytidine," *Antimicrob. Agents Chemotherapy* 43:2077–2080, American Society for Microbiology (Aug. 1999).

Southern, E.M., "Detection of Specific Sequences Among DNA Fragments Separated by Gel Electrophoresis," *J. Mol. Biol.* 98:503–517, Academic Press (1975).

Spedding, G. et al., "Inhibition of reverse transcriptases by flavonoids," *Antiviral Res.* 12:99–110, Elsevier Science Publishers B.V. (Biomedical Division) (1989).

Sugiura, W. et al., "Identification of Insertion Mutations in HIV–1 Reverse Transcriptase Causing Multiple Drug Resistance to Nucleoside Analogue Reverse Transcriptase Inhibitors," *J. Hum. Virol.* 2:146–153, Lippincott Williams & Wilkins, Inc. (May–Jun. 1999).

Sun, D. et al., "Cloning, expression, and purification of a catalytic fragment of Moloney murine leukemia virus reverse transcriptase: Crystallization of nucleic acid complexes," *Protein Sci.* 7:1575–1582, Cambridge University Press (Jul. 1998).

Tanese, N. et al., "Abortive Reverse Transcription by Mutants of Moloney Murine Leukemia Virus Deficient in the Reverse Transcriptase–Associated RNase H Function," *J. Virol.* 65:4387–4397, American Society for Microbiology (1991).

Trentin, B. et al., "Human T–cell Leukemia Virus Type 1 Reverse Transcriptase (RT) Origniates from the pro and pol Open Reading Frames and Requires the Presence of RT–RNase H (RH) and RT–RH–Integrase Proteins for its Activity," *J. Virol.* 72:6504–6510, American Society for Microbiology (Aug. 1998).

Veal, G.J. et al., "Sequence–specific RNase H cleavage of gag mRNA from HIV–1 infected cells by an antisense oligonucleotide in vitro," *Nucl. Acids Res.* 26:5670–5675, Oxford University Press (Dec. 1998).

Yadav, P.N.S. et al., "A Computer–assisted Analysis of Conserved Residues in the Three–dimensional Structures of the Polymerase Domains of *Escherichia coli* DNA Polymerase I and HIV–1 Reverse Transcriptase," *J. Biol. Chem.* 269:716–720, The American Society for Biochemistry and Molecular Biology, Inc. (1994).

Whiting, S.H. and Champoux, J.J., "Properties of Strand Displacement Synthesis by Moloney Murine Leukemia Virus Reverse Transcriptase: Mechanistic Implications," *J. Mol. Biol.* 278:559–577, Academic Press Limited (May 1998).

Wilson, J.E. et al., "Human Immunodeficiency Virus Type–1 Reverse Transcriptase. Contribution of Met–184 to Binding of Nucleoside 5'–Triphosphate," *J. Biol. Chem.* 271:13656–13662, The American Society for Biochemistry and Molecular Biology, Inc. (1996).

Wöhrl, B.M. et al., "Footprint Analysis of Replicating Murine Leukemia Virus Reverse Transcriptase," *Science* 267:96–99, The American Association for the Advancement of Science (1995).

Co–Pending U.S. patent application No. 09/845,157, Smith et al., filed May 1, 2001.

Co–Pending U.S. patent application No. 09/808,124, Potter et al., filed Mar. 15, 2001.

Co–Pending U.S. patent application No. 09/902,741, Chatterjee, D.K., filed Jul. 12, 2001.

"Complaint," dated Jan. 8, 2001, from *Invitrogen Corporation v. New England Biolabs, Inc.*, U.S. District Court, District of Massachusetts, Civil Action No. 01 CV 10038 WGY.

"Complaint," dated Feb. 15, 2001, from *Invitrogen Corporation v. Display Systems Biotech, Inc.*, U.S. District Court, Southern District of California.

"Stratagene's Memorandum in Opposition to Invitrogen's Motion for Preliminary Injunction and Memorandum in Support of Strategene's Motion for Leave to File an Additional Brief in Opposition to LTI's Motion for Preliminary Injunction . . . ," dated Feb. 27, 2001, with attached Exhibits A–N, from *Invitrogen Corporation v. Strategene Holding Corp., Strategene, Inc., and Biocrest Manufacturing, L.P.*, U.S. District Court, District of Delaware, Civil Action No. 00–620 (JJF).

"Clonetech's Reply in Support of Its Motion for Summary Judgment of Invalidity (Claim Indefiniteness) and in the Alternative for a Claim Construction, and Clontech's Opposition to Invitrogen's Cross–Motion for Summary Judgement," dated Mar. 14, 2001, with attached Exhibits I and J, from *Invitrogen Corporation v. Clontech Laboratories, Inc.*, U.S. District Court, District of Maryland, Southern Division, Civil Action Nos. AW 96–4080 and AW 00–1879.

"Order" and attached "Memorandum Opinion," dated May 4, 2001, from *Invitrogen Corporation v. Clontech Laboratories, Inc.*, U.S. District Court, District of Maryland, Southern Division, Civil Action Nos. AW 96–4080 and AW 00–1879.

"Clontech's Notice Pursuant to 35 U.S.C. § 282," dated May 10, 2001, from *Invitrogen Corporation v. Clontech Laboratories, Inc.*, U.S. Disrict Court, District of Maryland, Southern Division, Civil Action Nos. AW 96–4080 and AW 00–1879.

"Order" and attached "Memorandum Opinion," dated May 22, 2001, from *Invitrogen Corporation v. Clontech Laboratories, Inc.*, U.S. District Court, District of Maryland, Southern Division, Civil Action Nos. AW 96–4080 and AW 00–1879.

"Clontech's Supplemental Pretrial Order," dated May 25, 2001, from *Invitrogen Corporation v. Clontech Laboratories, Inc.*, U.S. District Court, District of Maryland, Southern Division, Civil Action No. AW 00–1879 (consolidated w/AW 96–4080).

"Order" dated May 25, 2001, from *Invitrogen Corporation v. Clontech Laboratories, Inc.*, U.S. District Court, District of Maryland, Southern Division, Civil Action Nos. AW 96–4080 and AW 00–1879.

"Reponsive Expert Statement of Joseph O. Falkinham, III," dated May 31, 2001, from *Clontech Laboratories, Inc. v. Life Techologies, Inc.*, U.S. District Court, District of Maryland, Southern Division, Civil Action No. AW 00–1879.

"Order" and attached "Memorandum Opinion," dated Jul. 6, 2001, from *Invitrogen Corporation v. Strategene Holding Corp. et al.*, U.S. District Court, District of Maryland, Southern Division, Civil Action No. AW 01–1168.

"Report and Recomendation Regarding Clarification of the Court's Orders Dated May 4, 2001 and May 24, 2001," dated Aug. 8, 2001, from *Invitrogen Corporation v. Clontech Laboratories, Inc.*, U.S. District Court, District of Maryland, Southern Division, Civil Action Nos. AW 96–4080 and AW 00–1879.

"Defendant Clontech Laboratories, Inc.'s Objections to the Special Master's Report and Recommendation Regarding Clarification of the Court's Orders Dated May 4, 2001 and May 24, 2001," dated Aug. 17, 2001, from *Invitrogen Corporation v. Clontech Laboratories, Inc.*, U.S. District Court, District of Maryland, Southern Division, Civil Action Nos. AW 96–4080 and AW 00–1879.

"Invitrogen Corporation's Objections to the Special Master's Report and Recommendation Regarding Clarification of the Court's Orders Dated May 4, 2001 and May 24, 2001," dated Aug. 22, 2001, from *Invitrogen Corporation v. Clontech Laboratories, Inc.*, U.S. District Court, District of Maryland, Southern Division, Civil Action Nos. AW 96–4080 and AW 00–1879.

"Defendant Clontech Laboratories, Inc.'s Response to Plaintiff Invitrogen Corporation's Objections to the Special Master's Report and Recommendation Regarding Clarification of the Court's Orders Dated May 4, 2001 and May 24, 2001," dated Aug. 31, 2001, from *Invitrogen Corporation v. Clontech Laboratories, Inc.*, U.S. District Court, District of Maryland, Southern Division, Civil Action Nos. AW 96–4080 and AW 00–1879.

"Complaint for Patent Infringement and Inducement to Infringe," dated Sep. 6, 2001, from *Invitrogen Corporation v. Toyobo Co., Ltd.*, U.S. District Court, Southern District of California, Civil Action No. 01 CV 1628 W (JFS).

"Clontech's Motion for Partial Summary Judgment of Invalidity (Claim Indefiniteness)," dated Sep. 27, 2001, from *Invitrogen Corporation v. Clontech Laboratories, Inc.*, U.S. District Court, District of Maryland, Southern Division, Civil Action Nos. AW 96–4080 and AW 00–1879.

"Brief of Defendants–Appellees," dated Oct. 5, 2001, from *Invitrogen Corporation v. Stratagene Holding Corp., Stratagene, Inc., and Biocrest Manufacturing, L.P.*, U.S. Court of Appeals for the Federal Circuit, Civil Action No. AW–01–1168.

"Order," dated Oct. 5, 2001, from *Invitrogen Corporation v. Clontech Laboratories, Inc.*, U.S. District Court, District of Maryland, Southern Division, Civil Action Nos. AW 96–4080 and AW 00–1879.

"Complaint," dated Oct. 17, 2001, from *Invitrogen Corporation v. Incyte Genomics, Inc.*, U.S. District Court, District of Delaware, Civil Action No. 01–692.

"Rebuttal Expert Statement of Joseph O. Falkinham, III," from *Clontech Laboratories, Inc. v. Life Technologies, Inc.*, U.S. District Court, District of Delaware, Civil Action No. 98–750 (SLR).

"Expert Statement of Joseph O. Falkinham, III," with attached Exhibits 1–3, from *Clontech Laboratories, Inc. v. Life Technologies, Inc.*, U.S. District Court, District of Delaware, Civil Action No. 98–750 (SLR).

"Answer," dated Nov. 21, 2001, from *Invitrogen Corporation v. Incyte Genomics, Inc.*, U.S. District Court, District of Delaware, Civil Action No. 01–692.

"Reply Memorandum in Support of Clontech's Motion for Partial Summry Judgement of Invalidity (Claim Indefiniteness) and Opposition to LTI's Motion for Partial Summary Judgment of Definiteness," dated Nov. 1, 2001, with attached Exhibits 1–3, from *Invitrogen Coroporation v. Clontech Laboratories, Inc.*, U.S. District Court, District of Maryland Southern Division, Civil Action No. AW 96–4080 and AW 00–1879.

"Clontech's Memorandum in Support of Its Motion for Partial Summary Judgment That the Claims of the Patents–in–suit are Invalid for Failing to Satisfy the Written Description Requirement of 35 U.S.C. § 112, First Paragraph," dated Dec. 28, 2001, from *Invitrogen Corporation v. Clontech Laboratories, Inc.*, U.S. District Court, District of Maryland, Southern Division, Civil Action Nos. AW 96–4080 and AW 00–1879.

DeStefano, J.J., et al., "Characterization of an RNase H deficient mutant of human immunodeficiency virus–1 reverse transcriptase having an aspartate to asparagine change at position 498," *Biochim. Biophys. Acta* 1219:380–388, Elsevier Science B.V. (Oct. 1994).

Krug, M.S., and Berger, S.L., "[33] First–Strand cDNA Synthesis Primed with Oligo(dT)," *Meth. Enzymol.* 152:316–325, Academic Press, Inc. (Sep. 1987).

Mölling, K., et al., "Association of Viral Reverse Transcriptase with an Enzyme degrading the RNA Moiety of RNA–DNA Hybrids," *Nature New Biology* 234:240–243, Macmillan Journals Ltd. (1971).

"Memorandum in Support of Clontech's Motion for a Summary Judgment of Invalidity (Claim Indefiniteness), or in the Alternative, Motion for a Claim Construction," dated Feb. 14, 2001, with attached exhibits A–H from *Invitrogen Corporation v. Clontech Laboratories, Inc.*, U.S. District Court for the District of Maryland, Southern Division, Civil Action No. AW–96–4080 and AW–00–1879.

"Report and Recommendation Regarding (1) Invitrogen Corporation's Motion for Partial Summary Judgment That the Work of Goff et al Is Not Prior Art to the Patents–In–Suit, (2) Clontech's Cross Motion for Summry Jugement That the Work of Goff et al Is Invalidationg [sic] Prior Art Under 35 U.S.C. § 102(g) or In Alternative Is Admissible Evidence at Trial, and (3) Clontech's Motion *In Limine* to Exclude Evidence of the Work of Goff et al at Trial for Prior Art," dated Jan. 15, 2002, from *Invitrogen Corporation v. Clontech Laboratories, Inc.*, U.S. District Court for the District of Maryland, Southern Division, Civil Action No. AW–96–4080 and AW–00–1879.

Letter to Philip G. Hampton, II, from Robert J. Koch, dated Jan. 31, 2002, regarding *Invitrogen Corporation v. Clontech Laboratories, Inc.*, Civil Action No. AW–96–4080 and AW–00–1879.

Letter to Philip G. Hampton, II, from Marc R. Labgold, dated Feb. 1, 2002, regarding *Invitrogen Corporation v. Clontech Laboratories, Inc.*, Civil Action No. AW–96–4080 and AW–00–1879.

*Invitrogen Corporation v. Stratagene Holding Corporation, Strategene, Inc., and Biocrest Manufacturing, L.P.*, 2002 U.S. App. Lexis 3613 (Fed. Cir. 2002).

Letter to Robert J. Koch from Philip G. Hampton, II, dated Feb. 21, 2002, regarding *Invitrogen Corporation v. Clontech Laboratories, Inc.*, Civil Action No. AW–96–4080 and AW–00–1879.

"Clontech's Reply Memorandum in Support of Its Motion for Partial Summary Judgment of Invalidity (Written Description) and Opposition to LTI's Motion for Partial Summary Judgment," dated Mar. 4, 2002, from *Invitrogen Corporation v. Clontech Laboratories, Inc.*, U.S. District Court for the District of Maryland, Southern Division, Civil Action No. AW–96–4080 and AW–00–1879.

"Order," dated Mar. 18, 2002, from *Invitrogen vs. Clontech Laboratories, Inc.* , U.S. District Court for the District of Maryland, Southern Division, Civil Action No. AW–96–4080 and AW–00–1879.

\* cited by examiner

```
                                                           .          .          .          .          .   1078
ATG ACC CTA AAT ATA GAA GAT GAG CAT CGG CTA CAT GAG ACC TCA AAA GAG CCA GAT GTT
MET Thr Leu Asn Ile Glu Asp Glu His Arg Leu His Glu Thr Ser Lys Glu Pro Asp Val

1138
TCT CTA GGG TCC ACA TGG CTG TCT GAT TTT CCT CAG GCC TGG GCG GAA ACC GGG GGC ATG
Ser Leu Gly Ser Thr Trp Leu Ser Asp Phe Pro Gln Ala Trp Ala Glu Thr Gly Gly MET

1198
GGA CTG GCA GTT CGC CAA GCT CCT CTG ATC ATA CCT CTG AAA GCA ACC TCT ACC CCC GTG
Gly Leu Ala Val Arg Gln Ala Pro Leu Ile Ile Pro Leu Lys Ala Thr Ser Thr Pro Val

1258
TCC ATA AAA CAA TAC CCC ATG TCA CAA GAA GCC AGA CTG GGG ATC AAG CCC CAC ATA CAG
Ser Ile Lys Gln Tyr Pro MET Ser Gln Glu Ala Arg Leu Gly Ile Lys Pro His Ile Gln

1318
AGA CTG TTG GAC CAG GGA ATA CTG GTA CCC TGC CAG TCC CCC TGG AAC ACG CCC CTG CTA
Arg Leu Leu Asp Gln Gly Ile Leu Val Pro Cys Gln Ser Pro Trp Asn Thr Pro Leu Leu

1378
CCC GTT AAG AAA CCA GGG ACT AAT GAT TAT AGG CCT GTC CAG GAT CTG AGA GAA GTC AAC
Pro Val Lys Lys Pro Gly Thr Asn Asp Tyr Arg Pro Val Gln Asp Leu Arg Glu Val Asn

1438
AAG CGG GTG GAA GAC ATC CAC CCC ACC GTG CCC AAC CCT TAC AAC CTC TTG AGC GGG CTC
Lys Arg Val Glu Asp Ile His Pro Thr Val Pro Asn Pro Tyr Asn Leu Leu Ser Gly Leu

1438
AAG CGG GTG GAA GAC ATC CAC CCC ACC GTG CCC AAC CCT TAC AAC CTC TTG AGC GGG CTC
Lys Arg Val Glu Asp Ile His Pro Thr Val Pro Asn Pro Tyr Asn Leu Leu Ser Gly Leu

1498
CCA CCG TCC CAC CAG TGG TAC ACT GTG CTT GAT TTA AAG GAT GCC TTT TTC TGC CTG AGA
Pro Pro Ser His Gln Trp Tyr Thr Val Leu Asp Leu Lys Asp Ala Phe Phe Cys Leu Arg
```

FIG.6A

```
                                                                    1558
CTC CAC CCC ACC AGT CAG CCT CTC TTC GCC TTT GAG TGG AGA GAT CCA GAG ATG GGA ATC
Leu His Pro Thr Ser Gln Pro Leu Phe Ala Phe Glu Trp Arg Asp Pro Glu MET Gly Ile

1618
TCA GGA CAA TTG ACC TGG ACC AGA CTC CCA CAG GGT TTC AAA AAC AGT CCC ACC CTG TTT
Ser Gly Gln Leu Thr Trp Thr Arg Leu Pro Gln Gly Phe Lys Asn Ser Pro Thr Leu Phe

1678
GAT GAG GCA CTG CAC AGA GAC CTA GCA GAC TTC CGG ATC CAG CAC CCA GAC TTG ATC CTG
Asp Glu Ala Leu His Arg Asp Leu Ala Asp Phe Arg Ile Gln His Pro Asp Leu Ile Leu

1738
CTA CAG TAC GTG GAT GAC TTA CTG CTG GCC GCC ACT TCT GAG CTA GAC TGC CAA CAA GGT
Leu Gln Tyr Val Asp Asp Leu Leu Leu Ala Ala Thr Ser Glu Leu Asp Cys Gln Gln Gly

1798
ACT CGG GCC CTG TTA CAA ACC CTA GGG AAC CTC GGG TAT CGG GCC TCG GCC AAG AAA GCC
Thr Arg Ala Leu Leu Gln Thr Leu Gly Asn Leu Gly Tyr Arg Ala Ser Ala Lys Lys Ala

1858
CAA ATT TGC CAG AAA CAG GTC AAG TAT CTG GGG TAT CTT CTA AAA GAG GGT CAG AGA TGG
Gln Ile Cys Gln Lys Gln Val Lys Tyr Leu Gly Tyr Leu Leu Lys Glu Gly Gln Arg Trp

1918
CTG ACT GAG GCC AGA AAA GAG ACT GTG ATG GGG CAG CCT ACT CCG AAG ACC CCT CGA CAA
Leu Thr Glu Ala Arg Lys Glu Thr Val MET Gly Gln Pro Thr Pro Lys Thr Pro Arg Gln

1978
CTA AGG GAG TTC CTA GGG ACG GCA GGC TTC TGT CGC CTC TGG ATC CCT GGG TTT GCA GAA
Leu Arg Glu Phe Leu Gly Thr Ala Gly Phe Cys Arg Leu Trp Ile Pro Gly Phe Ala Glu

2038
ATG GCA GCC CCC TTG TAC CCT CTC ACC AAA ACG GGG ACT CTG TTT AAT TGG GGC CCA GAC
MET Ala Ala Pro Leu Tyr Pro Leu Thr Lys Thr Gly Thr Leu Phe Asn Trp Gly Pro Asp
```

FIG.6B

```
                                                                          2098
CAA CAA AAG GCC TAT CAA GAA ATC AAG CAA GCT CTT CTA ACT GCC CCA GCC CTG GGG TTG
Gln Gln Lys Ala Tyr Gln Glu Ile Lys Gln Ala Leu Leu Thr Ala Pro Ala Leu Gly Leu

2158
CCA GAT TTG ACT AAG CCC TTT GAA CTC TTT GTC GAC GAG AAG CAG GGC TAC GCC AAA GGT
Pro Asp Leu Thr Lys Pro Phe Glu Leu Phe Val Asp Glu Lys Gln Gly Tyr Ala Lys Gly

2218
GTC CTA ACG CAA AAA CTG GGA CCT TGG CGT CGG CCG GTG GCC TAC CTG TCC AAA AAG CTA
Val Leu Thr Gln Lys Leu Gly Pro Trp Arg Arg Pro Val Ala Tyr Leu Ser Lys Lys Leu

2278
GAC CCA GTA GCA GCT GGG TGG CCC CCT TGC CTA CGG ATG GTA GCA GCC ATT GCC GTA CTG
Asp Pro Val Ala Ala Gly Trp Pro Pro Cys Leu Arg MET Val Ala Ala Ile Ala Val Leu

2338
ACA AAG GAT GCA GGC AAG CTA ACC ATG GGA CAG CCA CTA GTC ATT CTG GCC CCC CAT GCA
Thr Lys Asp Ala Gly Lys Leu Thr MET Gly Gln Pro Leu Val Ile Leu Ala Pro His Ala

2398
GTA GAG GCA CTA GTC AAA CAA CCC CCC GAC CGC TGG CTT TCC AAC GCC CGG ATG ACT CAC
Val Glu Ala Leu Val Lys Gln Pro Pro Asp Arg Trp Leu Ser Asn Ala Arg MET Thr His

2458
TAT CAG GCC TTG CTT TTG GAC ACG GAC CGG GTC CAG TTC GGA CCG GTG GTA GCC CTG AAC
Tyr Gln Ala Leu Leu Leu Asp Thr Asp Arg Val Gln Phe Gly Pro Val Val Ala Leu Asn

2518
CCG GCT ACG CTG CTC CCA CTG CCT GAG GAA GGG CTG CAA CAC AAC TGC CTT GAT AAT TCC
Pro Ala Thr Leu Leu Pro Leu Pro Glu Glu Gly Leu Gln His Asn Cys Leu Asp Asn Ser

2533
CGC TTA ATT AAT TAA
Arg Leu Ile Asn
```

FIG. 6C

CLONED GENES ENCODING REVERSE TRANSCRIPTASE LACKING RNASE H ACTIVITY

This application is a continuation of application Ser. No. 08/798,458, filed Feb. 10, 1997, which has issued as U.S. Pat. No. 6,063,608, which is a continuation of application Ser. No. 08/614,260, filed Mar. 12, 1996 (granted, U.S. Pat. No. 5,668,005), which is a continuation of application Ser. No. 08/404,907, filed Mar. 15, 1995 (abandoned), which is a continuation of application Ser. No. 07/825,260, filed Jan. 24, 1992 (granted, U.S. Pat. No. 5,405,776), which is a divisional of application Ser. No. 07/671,156, filed Mar. 18, 1991 (granted, U.S. Pat. No. 5,244,797), which is a continuation of application Ser. No. 07/143,396, filed Jan. 13, 1988 (abandoned).

FIELD OF THE INVENTION

The invention is in the field of recombinant genetics.

BACKGROUND OF THE INVENTION

Both viral and cloned reverse transcriptase (RT) contain at least two enzymatic activities, DNA polymerase and ribonuclease H (RNase H), that reside on a single polypeptide. Grandgenett, D. P. et al., *Proc. Natl. Acad. Sci. (USA)* 70:230–234 (1973); Moelling, K., *Virology* 62:46–59 (1974); Kotewicz, M. L., et al., *Gene* 35:249–258 (1985); and Roth, M. J., et al., *J. Biol. Chem.* 260:9326–9335 (1985). Little is known about the structure-functional relationship of these two activities, but such knowledge would be important both in understanding retroviral replication and in exploiting the enzyme as a recombinant DNA tool.

In the retrovirus life cycle, the RT DNA polymerase activity is responsible for transcribing viral RNA into double-stranded DNA. Varmus, H. (1982), in Weiss, R., et al. (eds.), *RNA Tumor Viruses*, Cold Spring Harbor Laboratory, pp. 410–423. The function of RNase H in replication is less clear, but it is thought to degrade genomic RNA during DNA synthesis to generate oligomeric RNA primers for plus-strand DNA synthesis, and to remove the RNA primers of both minus- and plus-strand DNA. Omer, C. A., et al., *Cell* 30:797–805 (1982); Resnick, R., et al., *J. Virol.* 51:813–821 (1984); Varmus, H. (1985), in Weiss, R., et al. (eds.), *RNA Tumor Viruses*, Cold Spring Harbor Laboratory, pp. 79–80.

The temporal relationship in vivo between DNA polymerization and RNA hydrolysis is not well defined. Furthermore, precisely how the two enzymatic activities are coordinated is not clear. Conditional mutations restricted to either DNA polymerase or RNase H would be invaluable in deciphering the events of retroviral replication. Unfortunately, conditional viral mutations in the RT gene invariably affect both activities. Lai, M. H. T, et al., *J. Virol.* 27:823–825 (1978); Moelling, K., et al., *J. Virol.* 32:370–378 (1979).

RT is used extensively in recombinant DNA technology to synthesize cDNA from mRNA. One major problem with cDNA synthesis is that the RNase H activity of RT degrades the mRNA template during first-strand synthesis. The mRNA poly(A)-oligo(dT) hybrid used as a primer for first-strand cDNA synthesis is degraded by RT RNase H. Thus, at the outset of cDNA synthesis, a competition is established between RNase H-mediated deadenylation of mRNA and initiation of DNA synthesis, which reduces the yield of cDNA product. Berger, S. L., et al., *Biochem.* 22:2365–2373 (1983). Furthermore, in some cases, the RNase H causes premature termination of DNA chain growth. Unfortunately, these events eliminate the potential for repeated copying of the RNA template.

Efforts to selectively inactivate RT RNase H with site-specific inhibitors have been unsuccessful (for review, see Gerard, G. F. (1983), in Jacob, S. T., (ed.), *Enzymes of Nucleic Acid Synthesis and Modification*, Vol. I, DNA Enzymes, CRC Press, Inc., Boca Raton, Fla., pp. 1–38). Attempts to physically separate the active centers of RT polymerase and RNase H activity by proteolysis have yielded a proteolytic fragment possessing only RNase H activity (Lai, M. H. T., et al., *J. Virol.* 25:652–663 (1978); Gerard, G. F., *J. Virol.* 26:16–28 (1978); and Gerard, G. F., *J. Virol.* 37:748–754 (1981)), but no corresponding fragment containing only polymerase activity has been isolated.

Computer analysis of the amino acid sequences from the putative gene products of retroviral pol genes has revealed a 150-residue segment at the carboxyl terminus that is homologous with the ribonuclease H of *E. coli* and a section close to the amino terminus which can be aligned with nonretroviral polymerases. Johnson, M. S., et al., *Proc. Natl. Acad. Sci. (USA)* 83:7648–7652 (1986). Based on these related amino acid sequences, Johnson et al. suggest that ribonuclease H activity should be situated at the carboxyl terminus, and the DNA polymerase activity at the amino terminus.

There have been a number of reports concerning the cloning of genes which encode RT and their expression in hosts. Weiss et al., U.S. Pat. No. 4,663,290 (1987); Gerard, G. F., DNA 5:271–279 (1986); Kotewicz, M. L., et al., *Gene* 35:249–258 (1985); Tanese, N., et al., *Proc. Natl. Acad. Sci. (USA)* 82:4944–4948 (1985); and Roth, M. J., et al., *J. Biol. Chem.* 260:9326–9335 (1985).

SUMMARY OF THE INVENTION

The invention relates to a gene which encodes reverse transcriptase having DNA polymerase activity and substantially no RNase H activity.

The invention also relates to a reverse transcriptase gene comprising the following DNA sequence:

```
                                                      1078 50
ATG ACC CTA AAT ATA GAA GAT GAG CAT CGG CTA CAT GAG ACC TCA AAA GAG CCA GAT GTT
MET Thr Leu Asn Ile Glu Asp Glu His Arg Leu His Glu Thr Ser Lys Glu Pro Asp Val

1138
TCT CTA GGG TCC ACA TGG CTG TCT GAT TTT CCT CAG GCC TGG GCG GAA ACC GGG GGC ATG
Ser Leu Gly Ser Thr Trp Leu Ser Asp Phe Pro Gln Ala Trp Ala Glu Thr Gly Gly MET

1198
GGA CTG GCA GTT CGC CAA GCT CCT CTG ATC ATA CCT CTG AAA GCA ACC TCT ACC CCC GTG
Gly Leu Ala Val Arg Gln Ala Pro Leu Ile Ile Pro Leu Lys Ala Thr Ser Thr Pro Val
```

-continued

```
                                                            1258
TCC ATA AAA CAA TAC CCC ATG TCA CAA GAA GCC AGA CTG GGG ATC AAG CCC CAC ATA CAG
Ser Ile Lys Gln Tyr Pro MET ser Gln Glu Ala Arg Leu Gly Ile Lys Pro His Ile Gln 1318
AGA CTG TTG GAC CAG GGA ATA CTG GTA CCC TGC CAG TCC CCC TGG AAC ACG CCC CTG CTA
Arg Leu Leu Asp Gln Gly Ile Leu Val Pro Cys Gln Ser Pro Trp Asn Thr Pro Leu Leu 1378
CCC GTT AAG AAA CCA GGG ACT AAT GAT TAT AGG CCT GTC CAG GAT CTG AGA GAA GTC AAC
Pro Val Lys Lys Pro Gly Thr Asn Asp Tyr Arg Pro Val Gln Asp Leu Arg Glu Val Asn 1438
AAG CGG GTG GAA GAC ATC CAC CCC ACC GTG CCC AAC CCT TAC AAC CTC TTG AGC GGG CTC
Lys Arg Val Glu Asp Ile His Pro Thr Val Pro Asn Pro Tyr Asn Leu Leu Ser Gly Leu 1498
CCA CCG TCC CAC CAG TGG TAC ACT GTG CTT GAT TTA AAG GAT GCC TTT TTC TGC CTG AGA
Pro Pro Ser His Gln Trp Tyr Thr Val Leu Asp Leu Lys Asp Ala Phe Phe Cys Leu Arg 1558
CTC CAC CCC ACC AGT CAG CCT CTC TTC GCC TTT GAG TGG AGA GAT CCA GAG ATG GGA ATC
Leu His Pro Thr Ser Gln Pro Leu Phe Ala Phe Glu Trp Arg Asp Pro Glu MET Gly Ile 1618
TCA GGA CAA TTG ACC TGG ACC AGA CTC CCA CAG GGT TTC AAA AAC AGT CCC ACC CTG TTT
Ser Gly Gln Leu Thr Trp Thr Arg Leu Pro Gln Gly Phe Lys Asn Ser Pro The Leu Phe 1678
GAT GAG GCA CTG CAC AGA GAC CTA GCA GAC TTC CGG ATC CAG CAC CCA GAC TTG ATC CTG
Asp Glu Ala Leu His Arg Asp Leu Ala Asp Phe Arg Ile Gln His Pro Asp Leu Ile Leu 1738
CTA CAG TAC GTG GAT GAC TTA CTG CTG GCC GCC ACT TCT GAG CTA GAC TGC CAA CAA GGT
Leu Gln Tyr Val Asp Asp Leu Leu Leu Ala Ala Thr Ser Glu Leu Asp Cys Gln Gln Gly 1798
ACT CGG GCC CTG TTA CAA ACC CTA GGG AAC CTC GGG TAT CGG GCC TCG GCC AAG AAA GCC
Thr Arg Ala Leu Leu Gln Thr Leu Gly Asn Leu Gly Tyr Arg Ala Ser Ala Lys Lys Ala 1858
CAA ATT TGC CAG AAA CAG GTC AAG TAT CTG GGG TAT CTT CTA AAA GAG GGT CAG AGA TGG
Gln Ile Cys Gln Lys Gln Val Lys Tyr Leu Gly Tyr Leu Leu Lys Glu Gly Gln Arg Trp 1918
CTG ACT GAG GCC AGA AAA GAG ACT GTG ATG GGG CAG CCT ACT CCG AAG ACC CCT CGA CAA
Leu Thr Glu Ala Arg Lys Glu Thr Val MET Gly Gln Pro Thr Pro Lys Thr Pro Arg Gln 1978
CTA AGG GAG TTC CTA GGG ACG GCA GGC TTC TGT CGC CTC TGG ATC CCT GGG TTT GCA GAA
Leu Arg Glu Phe Leu Gly Thr Ala Gly Phe Cys Arg Leu Trp Ile Pro Gly Phe Ala Glu 2038
ATG GCA GCC CCC TTG TAC CCT CTC ACC AAA ACG GGG ACT CTG TTT AAT TGG GGC CCA GAC
MET Ala Ala Pro Leu Tyr Pro Leu Thr Lys Thr Gly Thr Leu Phe Asn Trp Gly Pro Asp 2098
CAA CAA AAG GCC TAT CAA GAA ATC AAG CAA GCT CTT CTA ACT GCC CCA GCC CTG GGG TTG
Gln Gln Lys Ala Tyr Gln Glu Ile Lys Gln Ala Leu Leu Thr Ala Pro Ala Leu Gly Leu 2158
CCA GAT TTG ACT AAG CCC TTT GAA CTC TTT GTC GAC GAG AAG CAG GGC TAC GCC AAA GGT
Pro Asp Leu Thr Lys Pro Phe Glu Leu Phe Val Asp Glu Lys Gln Gly Tyr Ala Lys Gly 2218
GTC CTA ACG CAA AAA CTG GGA CCT TGG CGT CGG CCG GTG GCC TAC CTG TCC AAA AAG CTA
Val Leu Thr Gln Lys Leu Gly Pro Trp Arg Arg Pro Val Ala Tyr Leu Ser Lys Lys Leu 2278
GAC CCA GTA GCA GCT GGG TGG CCC CCT TGC CTA CGG ATG GTA GCA GCC ATT GCC GTA CTG
Asp Pro Val Ala Ala Gly Trp Pro Pro Cys Leu Arg MET Val Ala Ala Ile Ala Val Leu 2338
ACA AAG GAT GCA GGC AAG CTA ACC ATG GGA CAG CCA CTA GTC ATT CTG GCC CCC CAT GCA
Thr Lys Asp Ala Gly Lys Leu Thr MET Gly Gln Pro Leu Val Ile Leu Ala Pro His Ala 2398
GTA GAG GCA CTA GTC AAA CAA CCC CCC GAC CGC TGG CTT TCC AAC GCC CGG ATG ACT CAC
Val Glu Ala Leu Val Lys Gln Pro Pro Asp Arg Trp Leu Ser Asn Ala Arg MET Thr His
```

```
                                                         2458
TAT CAG GCC TTG CTT TTG GAC ACG GAC CGG GTC CAG TTC GGA CCG GTG GTA GCC CTG AAC
Tyr Gln Ala Leu Leu Leu Asp Thr Asp Arg Val Gln Phe Gly Pro Val Val Ala Leu Asn

2512
CCG GCT ACG CTG CTC CCA CTG CCT GAG GAA GGG CTG CAA CAC AAC TGC CTT GAT
Pro Ala Thr Leu Leu Pro Leu Pro Glu Glu Gly Leu Gln His Asn Cys Leu Asp
``` or the degenerate variants thereof.

The invention also relates to a reverse transcriptase gene comprising the following DNA sequence:

```
    .           .           .           .           .           1078
ATG ACC CTA AAT ATA GAA GAT GAG CAT CGG CTA CAT GAG ACC TCA AAA GAG CCA GAT GTT
MET Thr Leu Asn Ile Glu Asp Glu His Arg Leu His Glu Thr Ser Lys Glu Pro Asp Val

1138
TCT CTA GGG TCC ACA TGG CTG TCT GAT TTT CCT CAG GCC TGG GCG GAA ACC GGG GGC ATG
Ser Leu Gly Ser Thr Trp Leu Ser Asp Phe Pro Gln Ala Trp Ala Glu Thr Gly Gly MET

1198
GGA CTG GCA GTT CGC CAA GCT CCT CTG ATC ATA CCT CTG AAA GCA ACC TCT ACC CCC GTG
Gly Leu Ala Val Arg Gln Ala Pro Leu Ile Ile Pro Leu Lys Ala Thr Ser Thr Pro Val

1258
TCC ATA AAA CAA TAC CCC ATG TCA CAA GAA GCC AGA CTG GGA ATC AAG CCC CAC ATA CAG
Ser Ile Lys Gln Tyr Pro MET ser Gln Glu Ala Arg Leu Gly Ile Lys Pro His Ile Gln 1318
AGA CTG TTG GAC CAG GGA ATA CTG GTA CCC TGC CAG TCC CCC TGG AAC ACG CCC CTG CTA
Arg Leu Leu Asp Gln Gly Ile Leu Val Pro Cys Gln Ser Pro Trp Asn Thr Pro Leu Leu 1378
CCC GTT AAG AAA CCA GGG ACT AAT GAT TAT AGG CCT GTC CAG GAT CTG AGA GAA GTC AAC
Pro Val Lys Lys Pro Gly Thr Asn Asp Tyr Arg Pro Val Gln Asp Leu Arg Glu Val Asn 1438
AAG CGG GTG GAA GAC ATC CAC CCC ACC GTG CCC AAC CCT TAC AAC CTC TTG AGC GGG CTC
Lys Arg Val Glu Asp Ile His Pro Thr Val Pro Asn Pro Tyr Asn Leu Leu Ser Gly Leu 1498
CCA CCG TCC CAC CAG TGG TAC ACT GTG CTT GAT TTA AAG GAT GCC TTT TTC TGC CTG AGA
Pro Pro Ser His Gln Trp Tyr Thr Val Leu Asp Leu Lys Asp Ala Phe Phe Cys Leu Arg 1558
CTC CAC CCC ACC AGT CAG CCT CTC TTC GCG TTT GAG TGG AGA GAT CCA GAG ATG GGA ATC
Leu His Pro Thr Ser Gln Pro Leu Phe Ala Phe Glu Trp Arg Asp Pro Glu MET Gly Ile 1618
TCA GGA CAA TTG ACC TGG ACC AGA CTC CCA CAG GGT TTC AAA AAC AGT CCC ACC CTG TTT
Ser Gly Gln Leu Thr Trp Thr Arg Leu Pro Gln Gly Phe Lys Asn Ser Pro Thr Leu Phe 1678
GAT GAG GCA CTG CAC AGA GAC CTA GCA GAC TTC CGG ATC CAG CAC CCA GAC TTG ATC CTG
Asp Glu Ala Leu His Arg Asp Leu Ala Asp Phe Arg Ile Gln His Pro Asp Leu Ile Leu 1738
CTA CAG TAC GTG GAT GAC TTA CTG CTG GCC GCC ACT TCT GAG CTA GAC TGC CAA CAA GGT
Leu Gln Tyr Val Asp Asp Leu Leu Leu Ala Ala Thr Ser Glu Leu Asp Cys Gln Gln Gly 1798
ACT CGG GCC CTG TTA CAA ACC CTA GGG AAC CTC GGG TAT CGG GCC TCG GCC AAG AAA GCC
Thr Arg Ala Leu Leu Gln Thr Leu Gly Asn Leu Gly Tyr Arg Ala Ser Ala Lys Lys Ala 1858
CAA ATT TGC CAG AAA CAG GTC AAG TAT CTG GGG TAT CTT CTA AAA GAG GGT CAG AGA TGG
Gln Ile Cys Gln Lys Gln Val Lys Tyr Leu Gly Tyr Leu Leu Lys Glu Gly Gln Arg Trp 1918
CTG ACT GAG GCC AGA AAA GAG ACT GTG ATG GGG CAG CCT ACT CCG AAG ACC CCT CGA CAA
Leu Thr Glu Ala Arg Lys Glu Thr Val MET Gly Gln Pro Thr Pro Lys Thr Pro Arg Gln
```

```
                                                                        1978
CTA AGG GAG TTC CTA GGG ACG GCA GGC TTC TGT CGC CTC TGG ATC CCT GGG TTT GCA GAA
Leu Arg Glu Phe Leu Gly Thr Ala Gly Phe Cys Arg Leu Trp Ile Pro Gly Phe Ala Glu

2038
ATG GCA GCC CCC TTG TAC CCT CTC ACC AAA ACG GGG ACT CTG TTT AAT TGG GGC CCA GAC
MET Ala Ala Pro Leu Tyr Pro Leu Thr Lys Thr Gly Thr Leu Phe Asn Trp Gly Pro Asp

2098
CAA CAA AAG GCC TAT CAA GAA ATC AAG CAA GCT CTT CTA ACT GCC CCA GCC CTG GGG TTG
Gln Gln Lys Ala Tyr Gln Glu Ile Lys Gln Ala Leu Leu Thr Ala Pro Ala Leu Gly Leu

2158
CCA GAT TTG ACT AAG CCC TTT GAA CTC TTT GTC GAC GAG AAG CAG GGC TAC GCC AAA GGT
Pro Asp Leu Thr Lys Pro Phe Glu Leu Phe Val Asp Glu Lys Gln Gly Tyr Ala Lys Gly

2218
GTC CTA ACG CAA AAA CTG GGA CCT TGG CGT CGG CCG GTG GCC TAC CTG TCC AAA AAG CTA
Val Leu Thr Gln Lys Leu Gly Pro Trp Arg Arg Pro Val Ala Tyr Leu Ser Lys Lys Leu

2278
GAC CCA GTA GCA GCT GGG TGG CCC CCT TGC CTA CGG ATG GTA GCA GCC ATT GCC GTA CTG
Asp Pro Val Ala Ala Gly Trp Pro Pro Cys Leu Arg MET Val Ala Ala Ile Ala Val Leu

2338
ACA AAG GAT GCA GGC AAG CTA ACC ATG GGA CAG CCA CTA GTC ATT CTG GCC CCC CAT GCA
Thr Lys Asp Ala Gly Lys Leu Thr MET Gly Gln Pro Leu Val Ile Leu Ala Pro His Ala

2398
GTA GAG GCA CTA GTC AAA CAA CCC CCC GAC CGC TGG CTT TCC AAC GCC CGG ATG ACT CAC
Val Glu Ala Leu Val Lys Gln Pro Pro Asp Arg Trp Leu Ser Asn Ala Arg MET Thr His

2458
TAT CAG GCC TTG CTT TTG GAC ACG GAC CGG GTC CAG TTC GGA CCG GTG GTA GCC CTG AAC
Tyr Gln Ala Leu Leu Leu Asp Thr Asp Arg Val Gln Phe Gly Pro Val Val Ala Leu Asn

2518
CCG GCT ACG CTG CTC CCA CTG CCT GAG GAA GGG CTG CAA CAC AAC TGC CTT GAT ATT TCC
Pro Ala Thr Leu Leu Pro Leu Pro Glu Glu Gly Leu Gln His Asn Cys Leu Asp Ile Ser

2530
CGC TTA ATT AAT
Arg Leu Ile Asn
``` or the degenerate variants thereof.

The invention also relates to the vectors containing the gene of the invention, hosts transformed with the vectors of the invention, and the reverse transcriptase expressed by the transformed hosts of the invention.

The invention also relates to a fusion protein comprising a polypeptide having RNA-dependent DNA polymerase activity and substantially no RNase H activity and a second peptide selected from polypeptide proteins which stabilize the fusion protein and hydrophobic leader sequences.

The invention also relates to a method of producing reverse transcriptase having DNA polymerase activity and substantially no RNase H activity, comprising culturing transformed hosts of the invention under conditions which produce reverse transcriptase, and isolating the reverse transcriptase so produced.

The invention also relates to a method of preparing cDNA from mRNA comprising contacting mRNA with a polypeptide having RNA-dependent DNA polymerase activity and substantially no RNase H activity, and isolating the cDNA so produced.

The invention also relates to a kit for the preparation of cDNA from mRNA comprising a carrier being compartmentalized to receive in close confinement therein one or more containers, wherein (a) a first container contains reverse transcriptase having DNA polymerase activity and substantially no RNase H activity;

(b) a second container contains a buffer and the nucleoside triphosphates;

(c) a third container contains oligo(dT)primer; and (d) a fourth container contains control RNA.

The invention is related to the discovery that portions of the RT gene can be deleted to give a deletion mutant having DNA polymerase activity but no detectable RNase H activity. This purified mutant RT lacking RNase H activity can be used to effectively synthesize cDNA from mRNA.

Figures 5A, 5B:
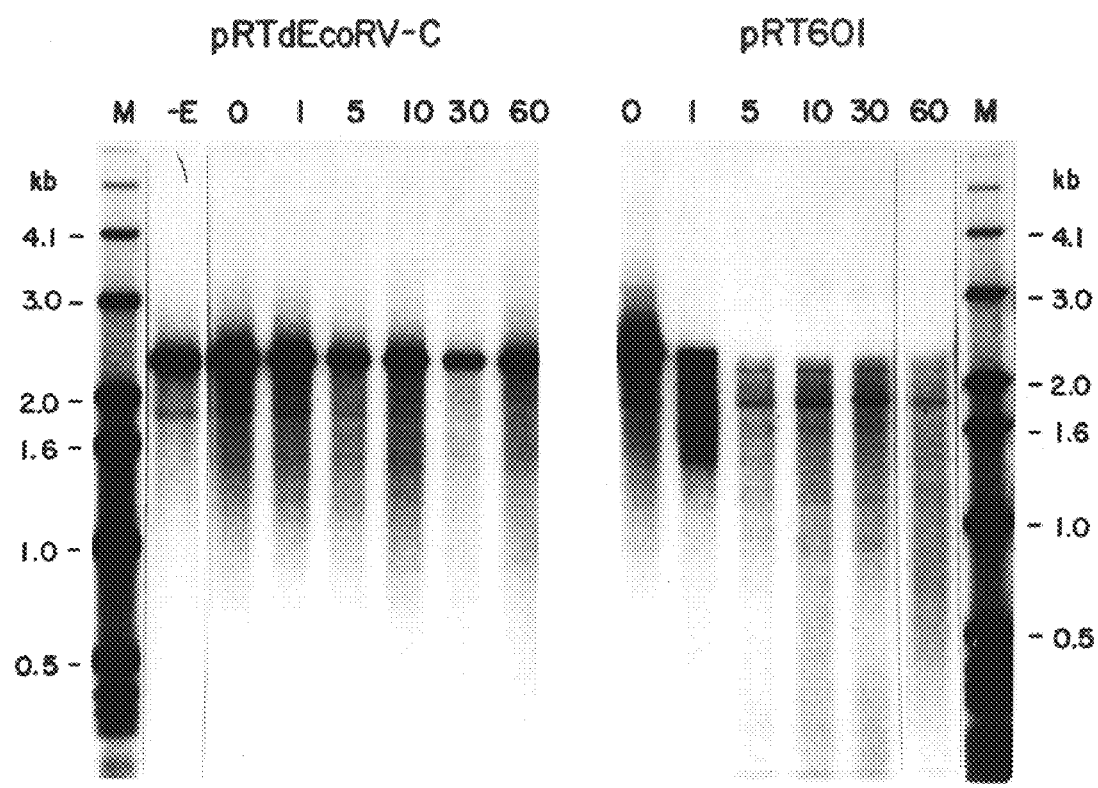

FIGS. 5A and 5B depict autoradiograms of $^{32}$P-labeled 2.3 kb poly(A)-tailed RNA after oligo(dT)primed cDNA synthesis catalyzed by pRTdEcoRV-C RT or pRT601 RT. Aliquots were removed from reaction mixtures containing no enzyme (−E) or 200 units of RT at the times indicated (in min). The minus enzyme control was incubated for 60 min. Samples were electrophoresed as described in Materials and Methods. A 1 kb ladder was used as marker (M).

FIGS. 6A, 6B and 6C depict the DNA sequence which encodes reverse transcriptase having DNA polymerase activity and substantially no RNase H activity. Also shown is the corresponding amino acid sequence.

DESCRIPTION OF THE PREFERRED EMBODIMENTS

The invention relates to the production of reverse transcriptase having DNA polymerase activity and substantially no RNase H activity, using recombinant DNA techniques.

Recombinant plasmids constructed as described herein provide reverse transcriptase for use in recombinant DNA technology to synthesize cDNA from mRNA without the problem associated with RNase H activity which degrades mRNA template during first-strand synthesis.

By the terms "substantially no RNase H activity" is intended reverse transcriptase purified to near homogeneity and having an RNase H activity of less than 0.001 pmoles $[^3H](A)_n$ solubilized per μg protein with a $[^3H](A)_n \cdot (dT)_n$ substrate in which the $[^3H](A)_n$ has a specific radioactivity of 2,200 cpm/pmole. RNase H activities of this specific activity or less allows the preparation of cDNA without significant degradation of the mRNA template during first-strand synthesis.

By the terms "degenerate variants" is intended cloned genes having variations of DNA sequence, but which encode the same amino acid sequence.

The reverse transcriptase gene (or the genetic information contained therein) can be obtained from a number of different sources. For instance, the gene may be obtained from eukaryotic cells which are infected with retrovirus, or from a number of plasmids which contain either a portion of or the entire retrovirus genome. In addition, messenger RNA-like RNA which contains the RT gene can be obtained from retroviruses. Examples of sources for RT include, but are not limited to, Moloney murine leukemia virus (M-MLV); human T-cell leukemia virus type I (HTLV-I); bovine leukemia virus (BLV); Rous Sarcoma Virus (RSV); human immunodeficiency virus (HIV); yeast, including Saccharomyces, Neurospora, Drosophila; primates; and rodents. See, for example, Weiss et al., U.S. Pat. No. 4,663,290 (1987); Gerard, G. R., *DNA* 5:271–279 (1986); Kotewicz, M. L., et al., *Gene* 35:249–258 (1985); Tanese, N., et al., *Proc. Natl. Acad. Sci. (USA)* 82:4944–4948 (1985); Roth, M. J., et al., *J. Biol. Chem.* 260:9326–9335 (1985); Michel, F., et al., *Nature* 316:641–643 (1985); Akins, R. A., et al., *Cell* 47:505–516 (1986), *EMBO J.* 4:1267–1275 (1985); and Fawcett, D. F., *Cell* 47:1007–1015 (1986).

RT proviral DNA can be isolated using standard isolation techniques. The DNA is cleaved into linear fragments, any one of which may contain the genes which encode RT. Such fragmentation can be achieved using enzymes which digest or cleave DNA, such as restriction enzymes which cleave DNA as specific base sequences. After the linear DNA fragments are generated, they are separated according to size by standard techniques. Such recombinant DNA techniques may be performed as described by Maniatis, T., et al., *Molecular Cloning: A Laboratory Manual*, Cold Spring Harbor Laboratory, Cold Spring Harbor, N.Y. (1982).

Identification of the DNA fragment which contains the gene may be accomplished in a number of ways. For example, it is possible to sequence the DNA fragments (Maxam and Gilbert, *Methods in Enzymology* 64:499 (1980); Messing, J., *Meth. in Enz.* 101C:20 (1983)) to identify which fragment contains the reverse transcriptase gene. Alternatively, hybridization techniques (Southern, *J. Mol. Biol.* 98:503 (1975)) using a labeled (e.g., radioactively labeled) DNA probe may be employed.

The fractions containing the desired DNA are pooled, ligated into a suitable vector, and used to transform a host. Screening for transformed hosts containing the RT gene may be accomplished by, for example, the method disclosed by Gerard et al., *Biochem.* 13:1632–1641 (1974) or by Gerard et al., *J. Virol.* 15:785–797 (1975). Alternatively, clones containing reverse transcriptase may be identified by hybridization with complementary labeled DNA.

An alternative to isolating the reverse transcriptase gene from a retroviral proviral DNA is to make cDNA to the mRNA-like RNA which codes for reverse transcriptase. To this end, mRNA-like RNA coding for reverse transcriptase is isolated from retrovirus. By standard techniques, the isolated mRNA is then converted into cDNA using reverse transcriptase. The cDNA can then be inserted into a plasmid vector in a conventional manner.

The choice of a suitable vector depends on a number of considerations known to one of ordinary skill in the art, such as the size of the fragment, nature of the host, number and position of restriction sites desired, and the selection marker and markers desired. Such vectors may include replicon and control sequences from species compatible with a host cell (see Maniatis et al., supra). Expression of the RT genes may also be placed under control of other regulatory sequences homologous or heterologous to the host organism in its untransformed state. For example, lactose-dependent *E. coli* chromosomal DNA comprises a lactose or lac operon which mediates lactose utilization by elaborating the enzyme β-galactosidase. The lac control elements may be obtained from bacteriophage lambda plac 5, which is infectious for *E. coli*. The lac promoter-operator system can be induced by IPTG.

Other promoter-operator systems or portions thereof can be employed as well. For example, galactose, alkaline phosphatase, tryptophan, xylose, tac, lambda pL, lambda pR and the like can be used. Once the vector or DNA sequence containing the constructs has been prepared, the vectors may be introduced into an appropriate host. Various techniques may be employed such as protoplast fusion, $CaCl_2$, calcium phosphate precipitation, electroporation, or other conventional DNA transfer techniques. The vectors may then be introduced into a second host by similar transfer methods, and also by cell to cell transfer methods such as conjugation. This cell-to-cell transfer may be accomplished using known techniques which depend upon the nature of the transferer bacterium, the recipient bacterium, and the cloning vector used to propagate the RT DNA. The transfer may require the use of a helper plasmid. See, for example, Ditta, G., et al., *Proc. Natl. Acad. Sci. (USA)* 77:7347–7351 (1980).

RT genes having DNA polymerase activity and substantially no RNase H activity may be obtained by deletion of deoxyribonucleotides at the 3' end of the gene which encode the portion of the polypeptide having RNase H activity. Deletions of the RT gene may be accomplished by cutting the plasmid at selected restriction sites within the RT gene and discarding the excised fragment. Further deletion of consecutive deoxyribonucleotides may be accomplished by treating the fragment with an exonuclease. The DNA ends may then be joined in such a way that the translation reading frame of the gene is maintained. The plasmid thus obtained may then be used to transform hosts which may then be screened for altered RT activity. RT RNase H activity may be assayed according to Gerard et al., *J. Virol.* 15:785–797 (1975). DNA polymerase activity may be assayed according to Gerard et al., *Biochem.* 13:1632–1641 (1974). Clones having DNA polymerase activity and substantially no RNase H activity may be used to prepare RT with altered activity.

According to these methods, the portion of the RT gene derived from M-MLV which encodes DNA polymerase was localized to about 1495 base pairs (about 1018 to about 2512) as shown in FIG. 6. The protein expressed by this gene has about 503 amino acids (FIG. 6). This protein has DNA polymerase activity and substantially no RNase H activity.

The invention also relates to fusion proteins which comprise the reverse transcriptase of the invention. Such fusion proteins may comprise, for example, a carrier protein which has a leader sequence of hydrophobic amino acids at the amino terminus of the reverse transcriptase. This carrier protein is normally excreted through the membrane of the cell within which it is made. By cleavage of the hydrophobic leader sequence during excretion, a means is provided for producing reverse transcriptase which can be recovered either.from the periplasmic space or the medium in which the bacterium is grown. The use of such a carrier protein allows isolation of reverse transcriptase without contamination by other proteins within the bacterium, and achieves production of a form of reverse transcriptase having greater stability by avoiding the enzymes within the bacterial cell which degrade foreign proteins. The DNA and amino acid sequences for such hydrophobic leader sequences, as well as methods of preparing such fusion proteins are taught, for example, by Gilbert et al., U.S. Pat. No. 4,411,994 (1983).

It is also possible to prepare fusion proteins comprising the reverse transcriptase of the invention which is substituted at the amino or carboxy termini with polypeptides which stabilize or change the solubility of the reverse transcriptase. An amino-terminal gene fusion which encodes reverse transcriptase, having both DNA polymerase and RNase activity, and trpE taught, for example, by Tanese, N. et al., *Proc. Nat'l. Acad. Sci.* 82:4944–4948 (1985). A carboxy-terminal gene fusion which encodes reverse transcriptase and part of the plasmid pBR322 tet gene is taught, for example, by Kotewicz, M., et al., *Gene* 35:249–258 (1985) and Gerard, G., *DNA* 5:271–279 (1986).

The transformed hosts of the invention may be cultured under protein producing conditions according to any of the methods which are known to those skilled in the art.

The reverse transcriptase having DNA polymerase activity and substantially no RNase activity may be isolated according to conventional methods known to those skilled in the art. For example, the cells may be collected by centrifugation, washed with suitable buffers, lysed, and the reverse transcriptase isolated by column chromatography, for example, on DEAE-cellulose, phosphocellulose (see Kotewicz et al., *Gene* 35:249–258 (1985)) or other standard isolation and identification techniques using, for example, polyribocytidylic acid-agarose, or hydroxylapatite or by electrophoresis or immunoprecipitation.

The reverse transcriptase so produced may be used to prepare cDNA from RNA by, for example, hybridizing an oligo(dT) primer or other complementary primers with the mRNA. The synthesis of a complete cDNA may be accomplished by adding the reverse transcriptase and all four deoxynucleoside triphosphates. Using the reverse transcriptase produced by the present invention allows for the preparation of cDNA from mRNA without concomitant degradation of the mRNA which results in incomplete cDNA synthesis. The resulting RNA-DNA hybrid may be treated, for example, with alkali or RNase H to selectively hydrolyze the RNA to leave cDNA which may be converted to double-stranded form in a second DNA reaction catalyzed by reverse transcriptase or other DNA polymerase. See Old, R. W., et al., *Principals of Gene Manirulation*, second edition, Studies in Microbiology, Vol. 2, University of California Press, p. 26 (1981).

The reverse transcriptase of the invention is ideally suited for incorporation into a kit for the preparation of cDNA from RNA. Such a kit may comprise a carrier means being compartmentalized to receive a close confinement therein, one or more container means, such as vials, tubes, and the like, each of said container means comprising one of the separate elements of the method used to prepare cDNA from RNA. For example, there may be provided a container means containing reverse transcriptase having DNA polymerase activity and substantially no RNase H activity, in solution. Further container means may contain suitable buffers, substrates for DNA synthesis such as the deoxynucleoside triphosphate, oligo(dT) primer, and control RNA for use as a standard.

The reverse transcriptase may be present in the solution at a concentration of 200 units/ml to 400 units/ml. The deoxynucleoside triphosphases may be present either in lyophilized form or as part of a buffer at a concentration of 0.5 mM to 2 mM. A suitable buffer, present at 5 times the final concentration of use, includes 250 mM Tris-HCl (pH 7.5 to 8.3), 375 mM KCl, 15 mM $MgCl_2$, and 50 mM dithiothreitol. The oligo (dT) may be present at a concentration of 5 µg/ml to 20 µg/ml. Control RNA, such as 2.3 kb control RNA, may be present at a concentration of 10 µg/ml to 20 µg/ml.

The following examples are illustrative but not limiting of the methods and compositions of the present invention. Any suitable modifications and adaptations which are obvious to one of ordinary skill in the art in recombinant DNA techniques are within the spirit and scope of the present invention.

EXAMPLES

Materials and Methods

Plasmids and Bacterial Strains

Figure 1:
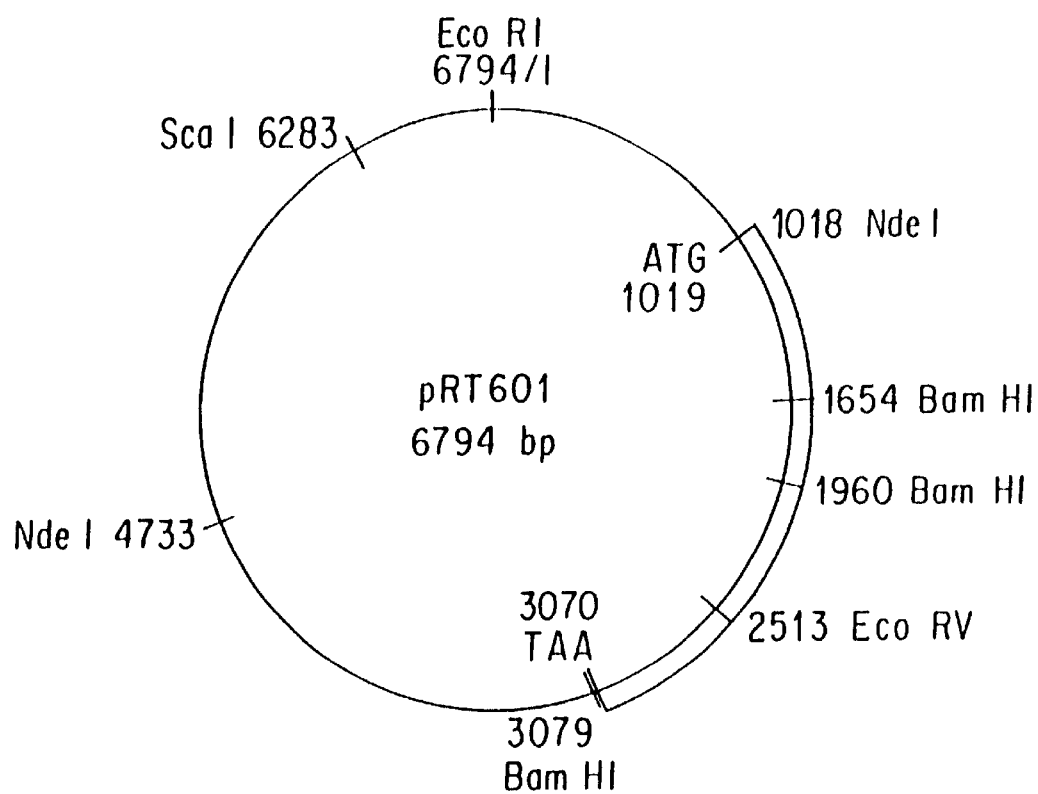
FIG. 1. This figure depicts the restriction map of plasmid pRT601. The M-MLV RT gene extends from position 1,019 to 3,070.

For deletion analysis of RT, a clone of M-MLV RT was constructed to overproduce stable RT in *Escherichia coli*, pRT601 (FIG. 1). Gerard, G. F., et al., *DNA* 5:271–279 (1986). It is a pBR322 replicon containing the strong lambda leftward promoter, pL, and the ribosome binding site of the lambda cII gene. (Higher copy number derivatives of pBR322, such as pUC plasmids, can also be used.) The coding sequence for the RT gene was carefully engineered into this plasmid to produce a protein with the amino terminus of the viral protein, and a carboxy terminus similar to the viral enzyme. Gerard, G. F., supra.

Two bacterial strains were used to propagate clones and express RT: K802 (Maniatis, T., et al., (1982), *Molecular Cloning: A Laboratory Handbook*, pp. 504–505, Cold Spring Harbor Laboratory, Cold Spring Harbor, N.Y.), made lysogenic for lambda cIindlts857 Sam7, and N4830 (Gottesman, M. E., et al., *J. Mol. Biol.* 140:57–75 (1980)), which contains a deleted a cryptic lambda prophage expressing the temperature sensitive cI allele indlts857. Bacteria were grown in super broth (SB) containing 2% tryptone, 1% yeast extract, 0.1% NaCl, pH 7.5, and 50 µg/ml ampicillin.

Plasmid Construction

Standard procedures for plasmid construction were performed as described previously (Kotewicz, M. L., et al., *Gene* 35:249–258 (1985); Gerard, G. F., et al., *DNA* 5:271–279 (1986)).

Temperature Induction of *E. coli* Carrying PRT601 and its Derivatives

Cultures of bacteria were grown in SB broth overnight at 32° C. and diluted 1:20 in fresh SB in the morning. The cells were grown at 32° C. until the $A_{590}$ was 0.8, and were induced by swirling in a 65° C. water bath until the temperature reached 42° C. Induction was continued for 30 minutes in a shaking water bath at 42° C., and then the cultures were incubated at 37° C. and grown an additional 30 minutes.

Preparation of Cell Extracts

Unless otherwise noted, all operations were performed at 4° C. Pelleted cells from one ml of culture were washed, lysed, and centrifuged as described previously (Kotewicz, M. L., supra). Supernatants were removed and assayed for RNase H and DNA polymerase activity.

Enzymes Assays

RT DNA polymerase activity in extracts was assayed specifically by using poly(2'-O-methylcytidylate)·oligodeoxyguanylate $[(Cm)_n \cdot (dG)_{12-18}]$ (Gerard, G. F., et al., *DNA* 5:271–279 (1986), eliminating interference from cellular DNA polymerases. To establish DNA polymerase specific activities of purified RT preparations, activity was assayed with $(A)_n \cdot (dT)_{12-18}$ (Houts, G. E., et al., *J. Virol.* 29:517–522 (1979) as described by Gerard, G. F., et al., *DNA* 5:271–279 (1986). One unit of DNA polymerase activity is the amount of enzyme that incorporates one nmole of deoxynucleoside monophosphate into acid insoluble product at 37° C. in 10 min.

RNase H activity in crude extracts and purified enzyme was assayed in reaction mixtures (50 µl) containing 50 mM Tris-HCl (pH 8.3), 2 mM $MnCl_2$, 1 mM dithiothreitol, and $[^3H](A)_n \cdot (dT)_n$ (5 µM $[^3H](A)_n$, 35 cpm/p-mole; 20 µM $(dT)_n$). Reactions were incubated at 37° C. for 20 min and were stopped by adding 10 µl of tRNA (1 mg/ml) and 20 µl of cold 50% TCA. After 10 minutes on ice, the mixture was centrifuged for 10 minutes in an Eppendorf centrifuge. Forty µl of the supernatant was counted in aqueous scintillant. One unit of RNase H activity is the amount of enzyme required to solubilize one mole of $[^3H](A)_n$ in $[^3H](A)_n \cdot (dT)_n$ in 10 min at 37° C.

Synthesis of Poly(A)-Tailed RNA

Synthetic 2.3 kb and 6.2 kb RNAs containing a 19 nucleotide poly(A) tail at the 3' end were synthesized with T7 RNA polymerase from Xba I-cut pJD2.3 and Hind III-cut pHL3X, respectively. Reaction mixtures (0.3 ml) contained 40 mM Tris-HCl (pH 8.0), 8 mM $MgCl_2$, 2 mM spermidine-HCl, 5 mM dithiothreitol, 0.4 mM each of CTP, UTP, GTP, and ATP, 20 µg/ml DNA, and 2,000 units/ml T7 RNA polymerase. Uniformly labeled RNA was synthesized with all four $[\alpha-^{32}P]NTPs$, each at 0.4 mM and 250 cpm/pmole. After 1 hr incubation at 37° C., the RNA product was phenol extracted, ethanol precipitated, and purified by oligo(dT)-cellulose chromatography to ensure the presence of a poly (A) tail.

Conditions for cDNA Synthesis

When assessing the effect of cDNA synthesis upon the integrity of template RNA, reaction mixtures (50 µl) contained 50 mM Tris-HCl (pH 8.3), 75 mM KCl, 3 mM $MgCl_2$, 10 mM dithiothreitol, 0.5 mM each dATP, dGTP, and dTTP, 0.5 mM $[^3H]dCTP$ (200 cpm/pmol), 50 µg/ml $(dT)_{12-18}$, 20 µg/ml 2.3 kb $[^{32}P]$labeled RNA, and 4,000 units/ml RT. The reactions were incubated at 37° C. and duplicate 2.5 µl aliquots were removed at 0, 1, 5, 10, 30, and 60 min. One aliquot was precipitated onto glass fiber filters using TCA to determine the amount of cDNA synthesized, and the other aliquot was prepared for glyoxal gel analysis. Carmichael, G. G., et al., *Method. Enzymol.* 65:380–391 (1980). The glyoxalated RNA was fractionated on a 1% agarose gel, dried, and autoradiographed. In some cases, 10 units of *E. coli* RNase H were added to the reaction mixture after 60 min and the incubation continued for 10 more min before aliquots were taken.

When measuring the ability of RT to synthesize a cDNA copy of long RNA, reaction mixtures (10 µl) contained the same buffer and salts, 0.5 mM each of dATP, dGTP, dTTP, and $[\alpha-^{32}P]dCTP$ (600 cpm/pmole), 50 µg/ml actinomycin D, 50 µg/ml $(dT)_{12-18}$, 100 µg/ml 6.2 kb poly(A)-tailed RNA, and 20,000 units/ml RT. After 1 hr at 37° C., the product in an aliquot (1 µl) was precipitated with TCA, counted, and the remaining DNA size fractionated on an alkaline 1.4% agarose gel according to McDonnel, M. W, et al., *J. Mol. Biol.* 110:119–146 (1977).

Purification of RT

Cells were grown to an $A_{590}$ of 3 in TYN and ampicillin medium (Gerard, G. F., et al., *DNA* 5:271–279 (1986)) at 30° C., induced at 43° C. for 45 min, and then grown at 36° C. for 3.5 hr before harvesting. RT was extracted from 100 g of cells as described (Gerard, G. F., supra) with the following exceptions. RT was precipitated by addition of solid $(NH_4)_2SO_4$ to 40% saturation. The $(NH_4)_2SO_4$ pellet was dissolved in 50 ml of 20 mM Tris-HCl (pH 7.5), 1 mM EDTA, 0.1 M NaCl, 5% glycerol, 1 mM dithiothreitol, and 0.01% n-octyl-β-D-glucopyranoside, the suspension was clarified by centrifugation at 10,000×g for 10 min, and the supernatant was desalted on a 320 ml (5×16 cm) Sephadex G-25 column run in buffer A (20 mM Tris-HCl, pH 7.5, 1 mM dithiothreitol, 1 mM EDTA, 5% glycerol, 0.01% NP-40) plus 0.1 M NaCl. After phosphocellulose chromatography, the RT peak was pooled, diluted with an equal volume of buffer A, and chromatographed on a 21-ml heparin-agarose column (1.5× 12 cm) equilibrated in buffer A plus 0.1 M NaCl. The RT peak from the heparinagarose column was chromatographed on a Mono-S HR 5/5 column equilibrated in buffer A (Gerard, G. F., supra).

RESULTS

Construction of Reverse Transcrintase Gene Deletions

Figure 2:
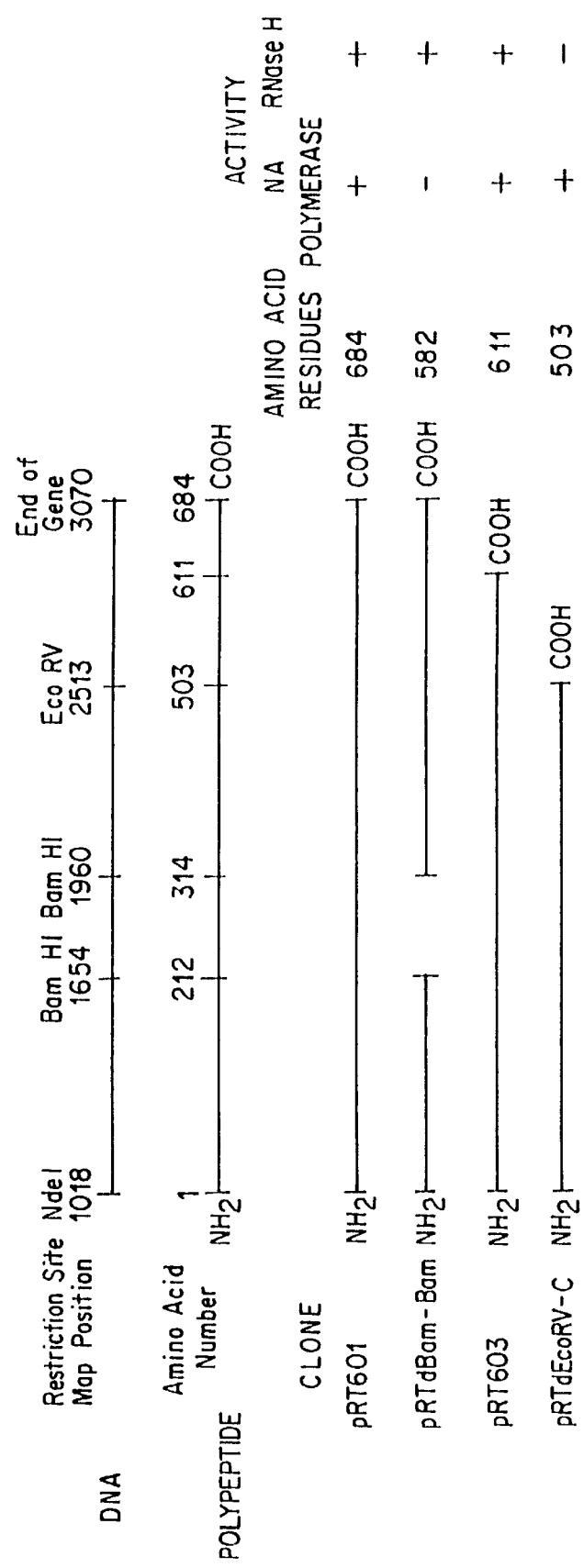
FIG. 2. This figure depicts schematic representation of pRT601 and related plasmids, and the enzymatic activities and predicted structure of the M-MLV RT protein coded by each plasmid.

Deletions of the M-MLV RT gene were constructed by cutting pRT601 (FIG. 1) at selected restriction sites within the RT gene, discarding the excised fragment, and joining the DNA ends in such a way that the translation reading frame of the gene was maintained. pRTdBam-Bam was constructed by deleting the Bam HI fragment between nucleotide positions 1,654 and 1,960 (FIGS. 1 and 2). Ligation of the Bam HI half sites at positions 1,654 and 1,960 maintained the translation reading frame across the site.

A deletion at the carboxy terminus of M-MLV RT (pRTdEcoRV-C) was constructed by deleting all of the 3' end of the gene downstream of the Eco RV site at position 2,513 (FIGS. 1 and 2). To construct pRTd-EcoRV-C, a Sca I (position 6,238) to Eco RV (position 2,513) fragment of pRT601 containing the 5' portion of the RT gene was ligated to a Sca I-Eco RI fragment derived from plasmid PBRT (Gerard, G. F., supra). The 3,211 base pair pBRT Sca I-Eco RI fragment contained the pBR322 origin of replication and a universal translation terminator sequence just inside the Eco RI site. The Eco RI site was repaired with DNA polymerase I Klenow fragment before ligation.

The plasmid of pRTdEcoRV-C was deposited in *E. coli* under the terms of the Budapest Treaty at the American Type Culture Collection (ATCC), Rockville, Md., and given accession number 67555.

pRT603 was constructed as described (Gerard, G. R., supra) which encodes an RT that contains 73 fewer amino acids than pRT601, all deleted from the carboxy terminus (FIG. 2).

DNA Polymerase and RNase H Levels in Cells Bearing Deletion Plasmids

Alteration of as little as 3 amino acids at the carboxy end of M-MLV RT can influence markedly the stability of the protein in *E. coli* (Gerard, G. F. supra). This must be taken into consideration in making correlations between cloned RT deletions and enzymatic activities in *E. coli* extracts. Both DNA polymerase and RNase H activity must be assayed and relative enzyme levels compared. For example, pRT603 codes for an RT with 73 fewer amino acids at the carboxy terminus than pRT601 RT (Gerard, G. F., supra; FIG. 2). The level of DNA polymerase activity in *E. coli* extracts of pRT603 RT is reduced 5 fold relative to pRT601. (Gerard, G. F. supra). However, the DNA polymerase and RNase H specific activities of purified pRT601 and pRT603 RT are comparable (Table 2). The reduced DNA polymerase activity in *E. coli* extracts of pRT603 RT is not due to a selective effect of the deletion on DNA polymerase activity, but rather to a reduction in the stability of pRT603 RT relative to pRT601 RT in cells ($t_{1/2}$ of 7 min versus 33 min) (Gerard, G. F. supra). Therefore, deletions within 70 amino acids of the RT carboxy terminus do not affect either RNase H or DNA polymerase activity.

In contrast, the DNA polymerase activity of pRTdBam-Bam RT was eliminated totally without affecting RNase H activity (Table 1) by the deletion of 102 amino acid residues between amino acids 212 and 314 (FIG. 2). Introduction of a more extensive deletion of 180 amino acids at the carboxy end of RT in pRTdEcoRV-C RT (FIG. 2) yielded extracts with RT DNA polymerase levels unchanged compared to pRT601 extracts, but with RNase H levels reduced 7.5 fold (Table 1). The residual RNase H activity in pRTdEcoRV-C extracts could be due to *E. coli* RNase H, the 5'→3' exonuclease of DNA polymerase I, or a small amount of residual RT-coded RNase H activity. To resolve this issue, pRTdEcoRV-C RT was purified and compared to RT encoded by pRT601.

Purification and Properties of DRTdEcoRV-C RT

Figure 3:
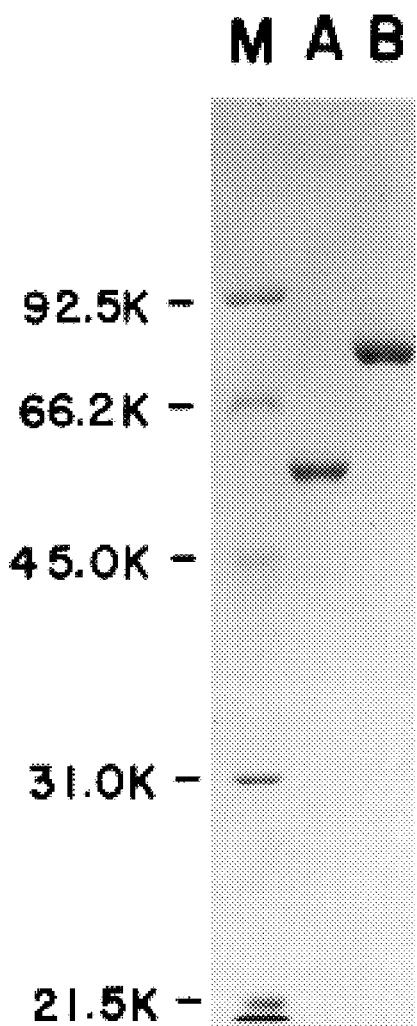
FIG. 3. This figure depicts an SDS-polyacrylamide gel of M-MLV RT. pRTdEcoRV-C RT (A) and pRT601 RT (B) (3 µg of each) were run on an SDS 10% polyacrylamide gel (Laemmli, U. K., *Nature* 227:680–685 (1970)). The gel was stained with Coomassie blue. Lane M contained Mr standards.

M-MLV reverse transcriptase encoded by pRTdEcoRV-C, pRT601, and pRT603 were purified as described in Materials and Methods. A summary of the purification of pRTdEcoRV-C RT is presented in Table 3. Three column steps produced a nearly homogeneous mutant enzyme with the same DNA polymerase specific activity as pRT601 RT with the template-primer $(Cm)_n \cdot (dG)_{12-18}$ (Table 2). With $(A)_n \cdot (dT)_{12-18}$, the mutant enzyme had one-fourth the DNA polymerase activity of pRT601 RT (Table 2). RNase H activity of purified pRTdEcoRV-C RT was undetectable using $[^3H](A)_n \cdot (dT)_n$ as the substrate. Most RNase H activity in extracts was eliminated from mutant RT by precipitation of the enzyme with 40% $(NH_4)_2SO_4$ (Table 3). Under these conditions, DNA polymerase I remains soluble (Richardson, C., et al., *J. Biol. Chem.* 239:222–230 (1964)), as does most of the RNase H activity in the extract. As judged by SDS-polyacrylamide gel electrophoresis, pRTdEcoRV-C RT purified through the Mono-S column was greater than 90% pure and had a molecular weight of 56,000 (FIG. 3), consistent with the molecular weight (57,000) predicted by the DNA sequence.

Figure 4:
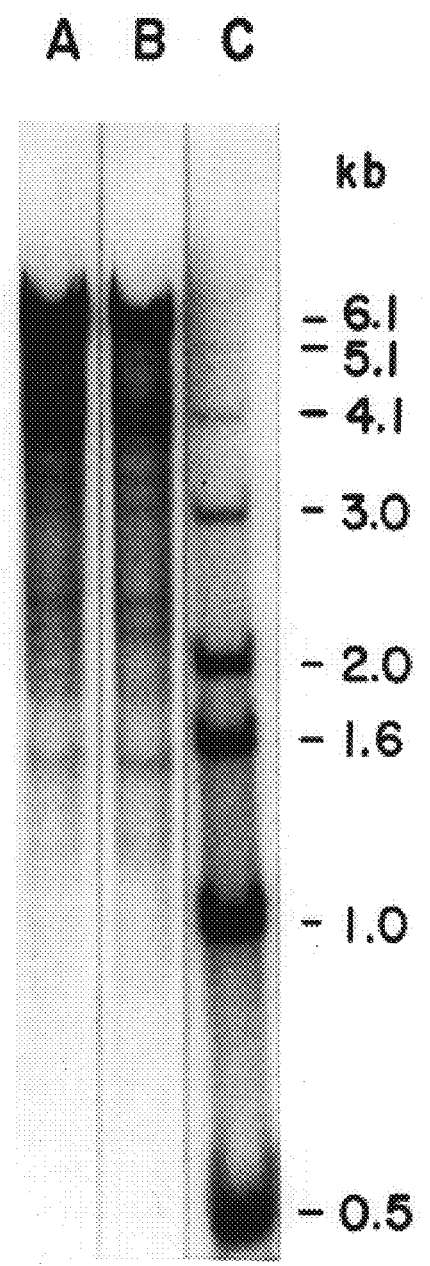
FIG. 4. This figure depicts an autoradiogram of $^{32}$P-labeled cDNA synthesized from 6.2 kb RNA (Materials and Methods) by pRTdEcoRV-C RT (A) or pRT601 RT (B). A 1 kb ladder was used as a standard (C). Electrophoresis was performed on an alkaline 1.4% agarose gel (McDonnel, M. W., et al., *J. Mol. Biol.* 110:119–146 (1977)).

A number of enzymatic properties of purified pRTdEcoRV-C RT and pRT601 RT were compared and were found to be similar. These included half life at 37° C., monovalent and divalent metal ion optima, fidelity of dNTP incorporation with homopolymer templates, and insensitivity to stimulation by polyanions. The abilities of the two enzymes to synthesize heteropolymeric DNA were also compared. FIG. 4 shows that pRTdEcoRV-C RT catalyzed the synthesis of full-length cDNA from 6.2 kb RNA more efficiently than pRT601 RT. The amount of cDNA synthesized from 1 µg of RNA was 0.28 µg (34% full-length) and 0.24 µg (24% full-length) with pRTdEcoRV-C RT and pRT601 RT, respectively.

To confirm that pRTdEcoRV-C RT completely lacked RNase H activity, the integrity of a uniformly $^{32}$P-labeled RNA template after conversion to hybrid form during RT-catalyzed DNA synthesis was examined. FIG. 5 shows that with pRT601 RT, the full-length 2.3 kb RNA template was degraded totally after 5 min of synthesis. In contrast, with pRTdEcoRV-C RT the RNA was intact even after 60 min. The amount of cDNA synthesized after 60 min from 1 µg of RNA was 0.67 and 0.76 µg with pRT601 and pRTdEcoRV-C RT, respectively. When 10 units of *E. coli* RNase H were added to the pRTdEcoRV-C RT reaction after 60 min of incubation, all of the RNA was degraded, confirming the hybrid state of the RNA. In addition, 15 µg (1,200 units) of pRTdEcoRV-C RT solubilized no radioactivity from a $[^3H](A)_n \cdot (dT)_n$ substrate in which the $[^3H](A)_n$ had a specific activity of 2,200 cpm/pmole (Materials and Methods).

Experiments with a frameshift mutant of MLV producing a 47K RT molecule truncated at the carboxy terminus (Levin, J. G. et al., *J. Virol.* 51:470–478 (1984)) and with antibodies to synthetic peptides modeled to Rous sarcoma virus pol gene sequences (Grandgenett, D. et al., *J. Biol. Chem.* 260:8243–8249 (1985)) suggest the RNase H activity of RT resides within the amino-terminal portion of the molecule. Conversely, the extensive homology found between the amino acids of *E. coli* RNase H and the 153-residue segment at the carboxy-terminal end of M-MLV RT (Johnson, M. S. et al. *Proc. Natl. Acad. Sci (USA)* 83:7648–7652 (1986)) suggests the RNase H activity resides within the carboxy-terminal portion of RT.

By deleting large segments (100 to 200 codons) of the M-MLV RT gene, the regions within the RT molecule responsible for DNA polymerase and RNase H activity have been identified. DNA polymerase was mapped to the amino half of the molecule, and RNase H to within 200 amino acids of the carboxy end, confirming the predictions based upon amino acid homology (Johnson, M. S. et al., supra). In this context, the results with one RT clone, pRT603 (FIG. 2), are of interest. The RT protein encoded by pRT603 is missing the carboxy half of the 153 amino acid segment of RT homologous to *E. coli* RNase H, which includes 20 of 48 homologous amino acids. Yet, pRT603 RT has normal levels of RNase H activity. These missing, homologous residues apparently are not required for catalysis, and might serve a nucleic acid binding or structural role. Consistent with the latter, a single amino acid change at a position 12 residues from the carboxy end of *E. coli* RNase H produces a 10-fold reduction in RNase H specific activity (Kanaya, S. et al., *J. Bacteriol.* 154:1021–1026 (1983)). This reduction appears to be the result of altered protein conformation (Kanaya, S. et al., supra).

If the RT polymerase and nuclease active sites reside on separate structural domains, it should be possible theoretically to isolate two separate protein fragments, each with a single activity. A 24K to 30K proteolytic fragment of RT possessing only RNase H activity has been isolated (Lai, M. H. T. et al., *J. Virol.* 25:652–663 (1978); Gerard, G. F., *J. Virol.* 26:16–28 (1978); Gerard, G. F., *J. Virol.* 37:748–754 (1981)), but unfortunately, the location of this RNase H fragment in the parent RT polypeptide has not been established, and no analogous DNA polymerase containing fragment has ever been found. The results presented here show that of the 684 amino acids in pRT601 RT, residues between amino acid 212 and 314 are required for DNA polymerase activity, and residues between amino acid 503 and 611 are required for RNase H activity. They also demonstrate for the first time that the RT DNA polymerase activity can exist independently of RNase H activity on an RT protein fragment. Purified pRTdEcoRV-C RT appeared to be totally devoid of RNase H activity, based upon two sensitive assays, and to have full DNA polymerase activity. However, these results do not rule out the possibility that the two active centers share a portion(s) of the RT molecule.

Demonstration of a separate structural domain for the RNase H active center was attempted by constructing two amino-terminal deletion derivatives of pRT601. The first derivative contained sequences for the Eco RV site at position 2513 to the 3' end of the RT gene (see FIG. 2), and the second contained sequences from an Nco I site at position 2302 to the 3' end of the RT gene. Unfortunately, neither clone produced detectable RNase H activity in *E. coli* crude extracts. Such negative results are difficult to interpret because the proteins might be unable to fold in an active form, or might be extremely labile.

$(dT)_{12-18}$ only one fourth as efficiently as the parent RT. The origin of this difference has not yet been established.

TABLE 1

DNA polymerase and RNase H activity in extracts of heat induced *E.coli* K802 (lambda) bearing pRT601 or one of its derivatives.

| Plasmid | DNA polymerase Activity[a] (cpm incorporated/ 2.5 µl extract) | RNase H Activity[b] (cpm solubilized/ 2.5 µl extract) |
|---|---|---|
| pRT601 | 10,977 | 2,020 |
| pRTdBam-Bam | 179 | 1,564 |
| pRTdEcoRV-C | 10,038 | 268 |

[a]Reverse transcriptase DNA polymerase activity was assayed with $(Cm)_n \cdot (dG)_{12-18}$ (Materials and Methods).
[b]RNase H activity assayed with $[^3H](A)_n \cdot (dT)_n$ (Materials and Methods).

TABLE 2

Comparison of activities of purified RT coded by pRT601, pRT603, and pRTdEcoRV-C

| Enzyme | DNA Polymerase Activity with | | RNase Acitivity (Units/mg) |
|---|---|---|---|
| | $(Cm)_n \cdot (dG)_{12-18}$ (Units/mg) | $(A)_n \cdot (dT)_{12-18}$ (Units/mg) | |
| pRT601 | 21,700 | 350,000 | 2,670 |
| pRT603 | ND[a] | 230,000 | 1,100 |
| pRTdEcoRV-C | 17,500 | 81,000 | —[b] |

[a]ND, not determined
[b]No activity was detected

TABLE 3

Summary of the purification of pRTdEcoRV-C RT

| Fraction | DNA Polymerase Activity[a] | | | | RNase H Activity | | |
|---|---|---|---|---|---|---|---|
| | Total Protein[c] (mg) | Total (Units) × 10³ | Specific Activity (Units/mg) × 10³ | Yield (%) | Total (Units) × 10³ | Specific Activity (Units/mg) × 10³ | Yield (%) |
| Crude lysate | 7,913 | 255 | 0.03 | 100 | 80 | 0.01 | 100 |
| Polymin P Supernatant | 2,735 | 323 | 0.12 | 127 | 157 | 0.06 | 196 |
| $(NH_4)_2SO_4$ pellet | 63 | 168 | 1.38 | 66 | 6.0 | 0.10 | 7 |
| Phosphocellulose pool | 8.8 | 167 | 19.0 | 66 | 2.0 | 0.23 | 3 |
| Heparin-agarose pool | 6.5 | 111 | 17.1 | 44 | —[b] | — | — |
| Mono S pool | 3.1 | 55 | 17.5 | 22 | —[b] | — | — |

[a]DNA polymerase activity was assayed with $(Cm)_n \cdot (dG)_{12-18}$
[b]No activity could be detected
[c]Protein concentrations were determined using bovine serum albumin as standard according to Lowry, O. H., et al., J. Biol. Chem. 239:222–230 (1964).

Deletion of the carboxy-terminal one-fourth of the M-MLV RT molecule did not disrupt the ability of the protein to fold in an active conformation. pRTdEcoRV-C RT copied heteropolymeric RNA more efficiently than intact RT. Yields of cDNA from 1 µg of 2.3 kb and 6.2 kb RNA were 0.76 µg (50% full-length) and 0.28 µg (34% full-length), respectively. Also, the truncated and intact enzymes had the same DNA polymerase specific activity with $(Cm)_n \cdot (dG)_{12-18}$. However, the truncated enzyme copied $(A)_n \cdot$

What is claimed is:
1. A composition, comprising
   (a) an mRNA template; and
   (b) a retroviral reverse transcriptase having DNA polymerase activity, wherein said reverse transcriptase allows the mRNA template to remain intact during a one minute cDNA synthesis reaction by said reverse transcriptase as determined by gel electrophoresis and wherein said reverse transcriptase is modified within the RNase H domain.

2. The composition of claim 1, wherein said reverse transcriptase is encoded by a modified nucleotide sequence that encodes a modified amino acid sequence modified in the region corresponding to amino acids 498–611 of M-MLV reverse transcriptase.

3. The composition of claim 1, wherein said reverse transcriptase is encoded by a modified nucleotide sequence that encodes a modified amino acid sequence modified in the region corresponding to amino acids 503–611 of M-MLV reverse transcriptase.

4. The composition of claim 1, wherein said reverse transcriptase allows the mRNA template to remain intact during a 5 minute cDNA synthesis reaction as determined by gel electrophoresis.

5. The composition of claim 1, wherein said reverse transcriptase allows the mRNA template to remain intact during a 10 minute cDNA synthesis reaction as determined by gel electrophoresis.

6. The composition of claim 1, wherein said reverse transcriptase allows the mRNA template to remain intact during a 30 minute cDNA synthesis reaction as determined by gel electrophoresis.

7. The composition of claim 1, wherein said reverse transcriptase allows the mRNA template to remain intact during a 60 minute cDNA synthesis reaction as determined by gel electrophoresis.

8. A composition, comprising
   (a) an mRNA template; and
   (b) an M-MLV reverse transcriptase having DNA polymerase activity, wherein said reverse transcriptase allows the mRNA template to remain intact during a one minute cDNA synthesis reaction by said reverse transcriptase as determined by gel electrophoresis and wherein said reverse transcriptase is modified within the RNase H domain.

9. The composition of claim 8, wherein said reverse transcriptase is encoded by a modified nucleotide sequence that encodes a modified amino acid sequence modified in the region of amino acids 498–611.

10. The composition of claim 8, wherein said reverse transcriptase is encoded by a modified nucleotide sequence that encodes a modified amino acid sequence modified in the region of amino acids 503–611.

11. The composition of claim 8, wherein said reverse transcriptase allows the mRNA template to remain intact during a 5 minute cDNA synthesis reaction as determined by gel electrophoresis.

12. The composition of claim 8, wherein said reverse transcriptase allows the mRNA template to remain intact during a 10 minute cDNA synthesis reaction as determined by gel electrophoresis.

13. The composition of claim 8, wherein said reverse transcriptase allows the mRNA template to remain intact during a 30 minute cDNA synthesis reaction as determined by gel electrophoresis.

14. The composition of claim 8, wherein said reverse transcriptase allows the mRNA template to remain intact during a 60 minute cDNA synthesis reaction as determined by gel electrophoresis.

15. A composition, comprising
   (a) an mRNA template; and
   (b) a retroviral reverse transcriptase having DNA polymerase activity, wherein said reverse transcriptase has no detectable RNase H activity as determined by examining by gel electrophoresis the integrity of an mRNA template during a one minute cDNA synthesis reaction by said reverse transcriptase and wherein said reverse transcriptase is modified within the RNase H domain.

16. The composition of claim 15, wherein said reverse transcriptase is encoded by a modified nucleotide sequence that encodes a modified amino acid sequence modified in the region corresponding to amino acids 498–611 of M-MLV reverse transcriptase.

17. The composition of claim 15, wherein said reverse transcriptase is encoded by a modified nucleotide sequence that encodes a modified amino acid sequence modified in the region corresponding to amino acids 503–611 of M-MLV reverse transcriptase.

18. The composition of claim 15, wherein said no detectable RNase H activity is determined by examining by gel electrophoresis the integrity of the mRNA template during a 5 minute cDNA synthesis reaction.

19. The composition of claim 15, wherein said no detectable RNase H activity is determined by examining by gel electrophoresis the integrity of the mRNA template during a 10 minute cDNA synthesis reaction.

20. The composition of claim 15, wherein said no detectable RNase H activity is determined by examining by gel electrophoresis the integrity of the mRNA template during a 30 minute cDNA synthesis reaction.

21. The composition of claim 15, wherein said no detectable RNase H activity is determined by examining by gel electrophoresis the integrity of the mRNA template during a 60 minute cDNA synthesis reaction.

22. A composition, comprising
   (a) an mRNA template; and
   (b) an M-MLV reverse transcriptase having DNA polymerase activity, wherein said reverse transcriptase has no detectable RNase H activity as determined by examining by gel electrophoresis the integrity of an mRNA template during a one minute cDNA synthesis reaction by said reverse transcriptase and wherein said reverse transcriptase is modified within the RNase H domain.

23. The composition of claim 22, wherein said reverse transcriptase is encoded by a modified nucleotide sequence that encodes a modified amino acid sequence modified in the region of amino acids 498–611.

24. The composition of claim 22, wherein said reverse transcriptase is encoded by a modified nucleotide sequence that encodes a modified amino acid sequence modified in the region of amino acids 503–611.

25. The composition of claim 22, wherein said no detectable RNase H activity is determined by examining by gel electrophoresis the integrity of the mRNA template during a 5 minute cDNA synthesis reaction.

26. The composition of claim 22, wherein said no detectable RNase H activity is determined by examining by gel electrophoresis the integrity of the mRNA template during a 10 minute cDNA synthesis reaction.

27. The composition of claim 22, wherein said no detectable RNase H activity is determined by examining by gel electrophoresis the integrity of the mRNA template during a 30 minute cDNA synthesis reaction.

28. The composition of claim 22, wherein said no detectable RNase H activity is determined by examining by gel electrophoresis the integrity of the mRNA template during a 60 minute cDNA synthesis reaction.

29. A composition, comprising
   (a) an mRNA template; and
   (b) a retroviral reverse transcriptase having DNA polymerase activity and $0.23 \times 10^3$ Units/mg or less of RNase H activity wherein said reverse transcriptase is modified within the RNase H domain.

30. The composition of claim 29, wherein said reverse transcriptase is encoded by a modified nucleotide sequence that encodes a modified amino acid sequence modified in the region corresponding to 498–611 of M-MLV reverse transcriptase.

31. The composition of claim 29, wherein said reverse transcriptase is encoded by a modified nucleotide sequence that encodes a modified amino acid sequence modified in the region corresponding to amino acids 503–611 of M-MLV reverse transcriptase.

32. The composition of claim 29, wherein said reverse transcriptase has $0.1 \times 10^3$ Units/mg or less of RNase H activity.

33. The composition of claim 29, wherein said reverse transcriptase has $0.01 \times 10^3$ Units/mg or less of RNase H activity.

34. The composition of claim 29, wherein said DNA polymerase activity is at least $17.5 \times 10^3$ Units/mg.

35. The composition of claim 29, wherein said DNA polymerase activity is at least $81 \times 10^3$ Units/mg.

36. A composition, comprising
(a) an mRNA template; and
(b) an M-MLV reverse transcriptase having DNA polymerase activity and $0.23 \times 10^3$ Units/mg or less of RNase H activity wherein said reverse transcriptase is modified within the RNase H domain.

37. The composition of claim 36, wherein said reverse transcriptase is encoded by a modified nucleotide sequence that encodes a modified amino acid sequence modified in the region of amino acids 498–611.

38. The composition of claim 36, wherein said reverse transcriptase is encoded by a modified nucleotide sequence that encodes a modified amino acid sequence modified in the region of amino acids 503–611.

39. The composition of claim 36, wherein said reverse transcriptase has $0.1 \times 10^3$ Units/mg or less of RNase H activity.

40. The composition of claim 36, wherein said reverse transcriptase has $0.01 \times 10^3$ Units/mg or less of RNase H activity.

41. The composition of claim 36, wherein said DNA polymerase activity is at least $17.5 \times 10^3$ Units/mg.

42. The composition of claim 36, wherein said DNA polymerase activity is at least $81 \times 10^3$ Units/mg.

43. A retroviral reverse transcriptase having DNA polymerase activity and less than 1,100 Units/mg RNase H activity wherein said reverse transcriptase is modified within the RNase H domain.

44. The reverse transcriptase of claim 43, wherein said reverse transcriptase is encoded by a modified nucleotide sequence that encodes a modified amino acid sequence modified in the region corresponding to amino acids 498–611 of M-MLV reverse transcriptase.

45. The reverse transcriptase of claim 43, wherein said reverse transcriptase is encoded by a modified nucleotide sequence that encodes a modified amino acid sequence modified in the region corresponding to amino acids 503–611 of M-MLV reverse transcriptase.

46. The reverse transcriptase of claim 43, wherein said reverse transcriptase may be used in the preparation of full-length cDNA.

47. The reverse transcriptase of claim 43, wherein said reverse transcriptase is a recombinantly produced reverse transcriptase.

48. The reverse transcriptase of claim 43, wherein said DNA polymerase activity is at least $81 \times 10^3$ Units/mg.

49. The reverse transcriptase of claim 43, wherein said DNA polymerase activity is at least $230 \times 10^3$ Units/mg.

50. The reverse transcriptase of claim 43, wherein said reverse transcriptase is isolated.

51. The reverse transcriptase of claim 43, wherein said reverse transcriptase is purified.

52. The reverse transcriptase of claim 43, wherein said reverse transcriptase is greater than 90% pure.

53. An M-MLV reverse transcriptase having DNA polymerase activity and less than 1,100 Units/mg RNase H activity wherein said reverse transcriptase is modified within the RNase H domain.

54. The reverse transcriptase of claim 53, wherein said reverse transcriptase is encoded by a modified nucleotide sequence that encodes a modified amino acid sequence modified in the region of amino acids 498–611.

55. The reverse transcriptase of claim 53, wherein said reverse transcriptase is encoded by a modified nucleotide sequence that encodes a modified amino acid sequence modified in the region of amino acids 503–611.

56. The reverse transcriptase of claim 53, wherein said reverse transcriptase may be used in the preparation of full-length cDNA.

57. The reverse transcriptase of claim 53, wherein said reverse transcriptase is a recombinantly produced reverse transcriptase.

58. The reverse transcriptase of claim 53, wherein said DNA polymerase activity is at least $81 \times 10^3$ Units/mg.

59. The reverse transcriptase of claim 53, wherein said DNA polymerase activity is at least $230 \times 10^3$ Units/mg.

60. The reverse transcriptase of claim 53, wherein said reverse transcriptase is isolated.

61. The reverse transcriptase of claim 53, wherein said reverse transcriptase is purified.

62. The reverse transcriptase of claim 53, wherein said reverse transcriptase is greater than 90% pure.

63. A retroviral reverse transcriptase having DNA polymerase activity of at least $17.5 \times 10^3$ Units/mg and less than 1,100 Units/mg RNase H activity wherein said reverse transcriptase is modified within the RNase H domain.

64. The reverse transcriptase of claim 63, wherein said reverse transcriptase is encoded by a modified nucleotide sequence that encodes a modified amino acid sequence modified in the region corresponding to amino acids 498–611 of M-MLV reverse transcriptase.

65. The reverse transcriptase of claim 63, wherein said reverse transcriptase is encoded by a modified nucleotide sequence that encodes a modified amino acid sequence modified in the region corresponding to amino acids 503–611 of M-MLV reverse transcriptase.

66. The reverse transcriptase of claim 63, wherein said reverse transcriptase may be used in the preparation of full-length cDNA.

67. The reverse transcriptase of claim 63, wherein said reverse transcriptase is a recombinantly produced reverse transcriptase.

68. The reverse transcriptase of claim 63, wherein said DNA polymerase activity is at least $81 \times 10^3$ Units/mg.

69. The reverse transcriptase of claim 63, wherein said DNA polymerase activity is at least $230 \times 10^3$ Units/mg.

70. The reverse transcriptase of claim 63, wherein said reverse transcriptase is isolated.

71. The reverse transcriptase of claim 63, wherein said reverse transcriptase is purified.

72. The reverse transcriptase of claim 63, wherein said reverse transcriptase is greater than 90% pure.

73. An M-MLV reverse transcriptase having DNA polymerase activity of at least $17.5 \times 10^3$ Units/mg and less than 1,100 Units/mg RNase H activity wherein said reverse transcriptase is modified within the RNase H domain.

74. The reverse transcriptase of claim 73, wherein said reverse transcriptase is encoded by a modified nucleotide sequence that encodes a modified amino acid sequence modified in the region of amino acids 498–611.

75. The reverse transcriptase of claim 73, wherein said reverse transcriptase is encoded by a modified nucleotide sequence that encodes a modified amino acid sequence modified in the region of amino acids 503–611.

76. The reverse transcriptase of claim 73, wherein said reverse transcriptase may be used in the preparation of full-length cDNA.

77. The reverse transcriptase of claim 73, wherein said reverse transcriptase is a recombinantly produced reverse transcriptase.

78. The reverse transcriptase of claim 73, wherein said DNA polymerase activity is at least $81 \times 10^3$ Units/mg.

79. The reverse transcriptase of claim 73, wherein said DNA polymerase activity is at least $230 \times 10^3$ Units/mg.

80. The reverse transcriptase of claim 73, wherein said reverse transcriptase is isolated.

81. The reverse transcriptase of claim 73, wherein said reverse transcriptase is purified.

82. The reverse transcriptase of claim 73, wherein said reverse transcriptase is greater than 90% pure.

83. A composition, comprising the reverse transcriptase of any one of claims 43–82.

84. The composition of claim 83, wherein said composition further comprises at least one component selected from the group consisting of one or more nucleoside triphosphates, an oligo(dT) primer, a buffer and an mRNA template.

85. A DNA molecule comprising a nucleotide sequence encoding the reverse transcriptase of any one of claims 42–49, 53–59, 63–69, and 73–79.

86. A vector comprising the DNA molecule of claim 85.

87. A host cell comprising the DNA molecule of claim 85.

88. The host cell of claim 87, wherein said host cell is *E. coli*.

89. A host cell comprising the vector of claim 86.

90. The host cell of claim 89, wherein said host cell is *E. coli*.

91. A method for preparing a DNA molecule, said method comprising:
    mixing an mRNA template with the reverse transcriptase of any one of claims 42–81; and
    incubating said mixture under conditions sufficient to make a first DNA molecule complementary to said mRNA template.

92. The method of claim 91, further comprising incubating said first DNA molecule under conditions sufficient to make a second DNA molecule complementary to said first DNA molecule.

93. The method of claim 91, wherein said first and second DNA molecule form a double stranded DNA molecule.

94. A method for producing a reverse transcriptase, said method comprising:
    culturing the host cell of claim 87 under conditions sufficient to produce said reverse transcriptase; and
    isolating or purifying said reverse transcriptase.

95. The method of claim 94, wherein said reverse transcriptase is isolated using column chromatography.

96. The method of claim 94, wherein said reverse transcriptase is greater than 90% pure.

97. A kit for the preparation of cDNA, said kit comprising a container containing the reverse transcriptase of any one of claims 42–81.

98. The kit of claim 97, said kit further comprising one or more additional containers selected from the group consisting of:
    a container containing one or more nucleoside triphosphates;
    a container containing an oligo(dT) primer; and
    a container containing a buffer suitable for use in making cDNA.

* * * * *

UNITED STATES PATENT AND TRADEMARK OFFICE
CERTIFICATE OF CORRECTION

PATENT NO. : 6,610,522 B1
DATED : August 26, 2003
INVENTOR(S) : Kotewicz et al.

It is certified that error appears in the above-identified patent and that said Letters Patent is hereby corrected as shown below:

Title page,
Item [56], References Cited, OTHER PUBLICATIONS,
"Hizi, A., et al.," reference, please delete "yype" and insert therein -- type --.
"Meloun, B., et al.," reference, please delete "*Thermoatinomyces*" and insert therein
-- *Thermoactinomyces*--.
"Brewer, L.C." reference, please delete "Independent" and insert therein -- Independence --.
"Meyers, J.C." reference, please delete "tanscriptase" and insert therein -- transcriptase --.
"Rho, H.M. and Gallo, R.C.," reference, please delete "RNAase" and insert therein
-- RNase --.
"Letter dated Oct. 9, 1987" reference, please delete "Disrict" and insert therein -- District --.
"Consent Judgment" reference, please delete "*Strategene*" and insert therein -- *Stratagene* --.
"Memorandum Opinion" reference, please delete "*Strategene*" and insert therein
-- *Stratagene* --.
"Memorandum Opinion" reference, please delete "Disrict" and insert therein -- District --.
"Strategene's Responses" reference, please delete "Strategene's" and insert therein
-- Stratagene's --
"Gerard, G.F. et al.," reference, please delete "Rnase" and insert therein -- RNase --.
"Freeman-Wittig, M.—J. et al.," reference, please delete "Diferential" and insert therein
-- Differential --.
"Freeman-Wittig, M—J. et al.," reference, please delete "Trancriptase" and insert therein
-- Transcriptase --.
"Grandgenett, D. et al.," reference, please delete "Activiation" and insert therein
-- Activation --.
"Gerard, G.," reference, please delete "Transriptase" and insert therein -- Transcriptase --.
"Gerard, G.," reference, please delete "*Clometech*" and insert therein -- *Clontech* --.
"Modak, M.J." reference, please delete "Inhibiton" and insert therein -- Inhibition --.
"Schatz, O. et al.," reference, please delete "RNAse" and insert therein -- RNase --.
"Zhan, X. et al.," reference, please delete "Luekemia" and insert therein -- Leukemia --.
"Defendant's Notice" reference, please delete "*Clonetech*" and insert therein -- *Clontech* --.
"Grandgenett, D. P. et al." reference, please delete "Myelobastosis" and insert therein
-- Myeloblastosis --.
"Moelling, K.," reference, please delete "Transriptase" and insert therein -- Transcriptase --.
"Toh, H. et al.," reference, please delete "polymerse" and insert therein -- polymerase --.
"Defendant's Exhibit No. 433" reference, please delete "Disrict" and insert therein
-- District --.
"DeStefano, J.J. et al.," reference, please delete "Rnase" and insert therein -- RNase --.
"DeStefano, J.J. et al.," reference, please delete "leukemia" and insert -- leukemia --.
"Myers, J.C. et al.," reference, please delete "meyloblastosis" and insert therein -- myeloblastosis --.
"Wang, L.—H." reference, please delete "RNAse" and insert therein -- RNase --.

UNITED STATES PATENT AND TRADEMARK OFFICE
CERTIFICATE OF CORRECTION

PATENT NO.    : 6,610,522 B1
DATED         : August 26, 2003
INVENTOR(S)   : Kotewicz et al.

It is certified that error appears in the above-identified patent and that said Letters Patent is hereby corrected as shown below:

Title page (cont'd),
"Ben-Artzi, H. et al.," reference, please delete "RNAse" and insert therein -- RNase --.
"Ben-Artzi, H. et al.," reference, please delete "Unversity" and insert therein -- University --.
"Chen, Y." reference, please delete "Hepadnaivruses" and insert therein -- Hepadnaviruses --.
"Lavingnon, M. et al.," reference, please delete "Transcriptse" and insert therein -- Transcriptase --.
"Post, K. et al.," reference, please delete "Replaement" and insert therein -- Replacement --.
"Rodgers, D.W. et al.," reference, please delete "(1985)" and insert therein -- (1995) --.
"Sarafianos, S.G. et al.," reference, please delete "transriptase" and insert therein -- transcriptase --.
"Smith, C.M. et al.," reference, please delete "Reuirements" and insert therein -- Requirements --.
"Trentin, B. et al.," reference, please delete "Origniates" and insert therein -- Originates --.
"Stratagene's Memorandum" reference, please delete "Strategene's" and insert therein -- Stratagene's --.
"Stratagene's Memorandum" reference, please delete "*Strategene*" and insert therein -- *Stratagene* --.
"Stratagene's Memorandum" reference, please delete "*Strategene*" and insert therein -- *Stratagene* --.
"Clonetech's Reply" reference, please delete "Clonetech's" and insert therein -- Clontech's --.
"Clonetech's Notice" reference, please delete "Disrict" and insert therein -- District --.
"Reponsive Expert Statement" reference, please delete "Reponsive" and insert therein -- Responsive --.
"Reponsive Expert Statement" reference, please delete "*Techologies*" and insert therein -- *Technologies* --.
"Order" reference, please delete "*Strategene*" and insert therein -- *Stratagene* --.
"Report" reference, please delete "Recomendation" and insert therein -- Recommendation --.
"Reply Memorandum" reference, please delete "*Summry*" and insert therein -- Summary --.
"Reply Memorandum" reference, please delete "*Coroporation*" and insert therein -- *Corporation* --.
"Report and Recommendation" reference, please delete "Summry Jugement" and insert -- Summary Judgment --.
"Invitrogen Corporation" reference, please delete "*Strategene*" and insert therein -- *Stratagene* --.

Column 9,
Line 67, please delete "as" and insert therein -- at --.

Column 10,
Line 60, please delete "transferer" and insert therein -- transferrer --.

Column 12,
Line 15, please delete "*Manirulation*" and insert therein -- *Manipulation* --.
Line 34, please delete "triphosphases" and insert therein -- triphosphates --.

UNITED STATES PATENT AND TRADEMARK OFFICE
CERTIFICATE OF CORRECTION

PATENT NO. : 6,610,522 B1
DATED : August 26, 2003
INVENTOR(S) : Kotewicz et al.

It is certified that error appears in the above-identified patent and that said Letters Patent is hereby corrected as shown below:

Column 13,
Line 4, please delete "a" between "deleted" and "cryptic".

Column 14,
Line 52, please delete "Transcrintase" and insert therein -- Transcriptase --.

Column 15,
Line 53, please delete "DRTdEcoRV-C" and insert therein -- pRTdEcoRV-C --.

Column 18,
Table 2, fourth column header, please delete "Activity" and insert therein -- Activity --.

Column 21,
Line 2, please insert -- amino acids -- between "to" and "498-611".

Column 23,
Line 32, please delete "42-49" and insert therein -- 43-49 --.

Column 24,
Line 6, please delete "42-81" and insert therein -- 43-82 --.
Line 14, please delete "91" and insert therein -- 92 --.
Line 27, please delete "42-81" and insert therein -- 43-82 --.

Signed and Sealed this

Second Day of November, 2004

JON W. DUDAS
*Director of the United States Patent and Trademark Office*